(12) United States Patent
Fredriksson et al.

(10) Patent No.: US 7,914,987 B2
(45) Date of Patent: Mar. 29, 2011

(54) METHODS AND COMPOSITIONS FOR USE IN ANALYTE DETECTION USING PROXIMITY PROBES

(75) Inventors: Simon Fredriksson, Palo Alto, CA (US); Ronald W. Davis, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 430 days.

(21) Appl. No.: 11/596,831

(22) PCT Filed: Jun. 14, 2005

(86) PCT No.: PCT/US2005/021058
§ 371 (c)(1),
(2), (4) Date: Aug. 28, 2008

(87) PCT Pub. No.: WO2005/123963
PCT Pub. Date: Dec. 29, 2005

(65) Prior Publication Data
US 2009/0162840 A1 Jun. 25, 2009

Related U.S. Application Data

(60) Provisional application No. 60/579,901, filed on Jun. 14, 2004.

(51) Int. Cl.
*C12Q 1/68* (2006.01)
*C12P 19/34* (2006.01)
*C07H 21/02* (2006.01)
(52) U.S. Cl. ........... 435/6; 435/91.2; 536/24.31; 536/24
(58) Field of Classification Search ............. 435/6, 91.2; 536/24.33, 24.31, 24.32
See application file for complete search history.

(56) References Cited

U.S. PATENT DOCUMENTS

| 5,635,602 | A | 6/1997 | Cantor et al. | |
|---|---|---|---|---|
| 5,849,878 | A | 12/1998 | Cantor et al. | |
| 6,511,809 | B2 * | 1/2003 | Baez et al. | 435/6 |
| 6,558,928 | B1 | 5/2003 | Landegren | |
| 2002/0064779 | A1 * | 5/2002 | Landegren et al. | 435/6 |
| 2004/0248103 | A1 * | 12/2004 | Feaver et al. | 435/6 |

FOREIGN PATENT DOCUMENTS

| WO | 97/00446 | 1/1997 |
|---|---|---|
| WO | WO 9700446 A1 * | 1/1997 |
| WO | 01/61037 | 8/2001 |
| WO | 03/044231 | 5/2003 |

OTHER PUBLICATIONS

Gullberg, M et al. A sense of closeness; protein detection by proximity ligation. Current Opinion in Biotechnol., vol. 14, pp. 82-86, 2003.*
Fredriksson et al., "Protein detection using proximity-dependent DNA ligation assays", Research Article, Nature Biotechnology, May 2002, vol. 20, pp. 473-477.
Gullberg et al., "A sense of closeness: protein detection by proximity ligation", Current Opinion, 2003, 14:82-86.
Gullberg et al., "Cytokine detection by antibody-based proximity ligation", PNAS, Jun. 1, 2004, vol. 101, No. 22, pp. 8420-8424.

* cited by examiner

*Primary Examiner* — Suryaprabha Chunduru
(74) *Attorney, Agent, or Firm* — Bozicevic, Field & Francis LLP; Bret E. Field; Elizabeth A. Alcamo

(57) ABSTRACT

Methods and compositions for detecting an analyte in a sample are provided. In practicing the subject methods, a sample is combined with at least a pair of proximity probes that each include an analyte binding domain and a nucleic acid domain. The resultant mixture is then contacted with a pair of asymmetric nucleic acid connectors. Proximity dependent connector mediated interaction between the nucleic acid domains of the proximity probes is then detected to determine the presence of the analyte in the sample. Also provided are kits and systems for practicing the subject methods.

33 Claims, 7 Drawing Sheets

FIG. 1
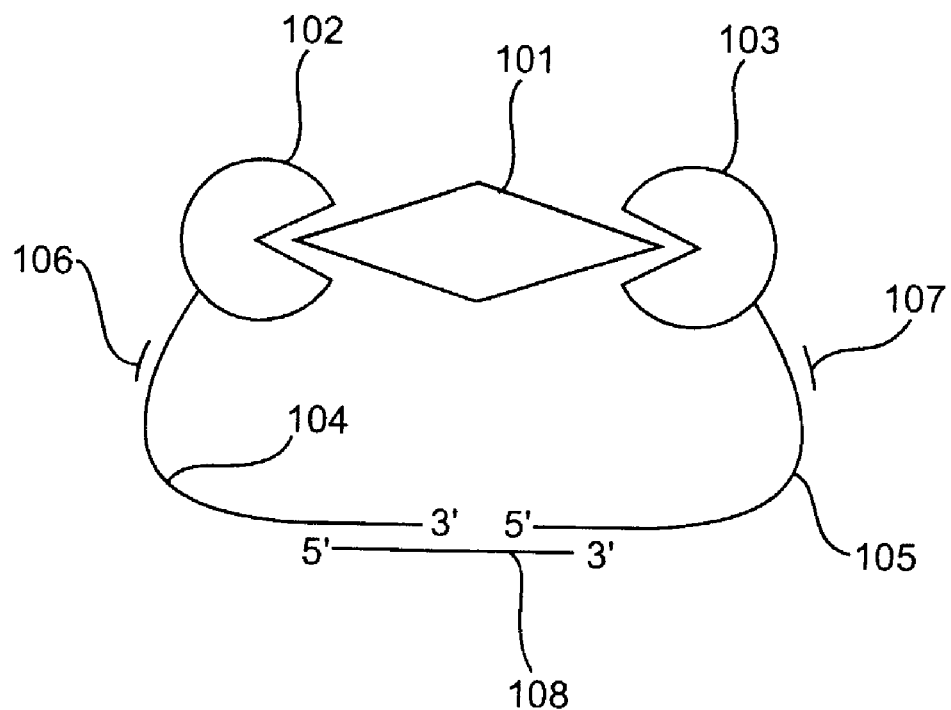
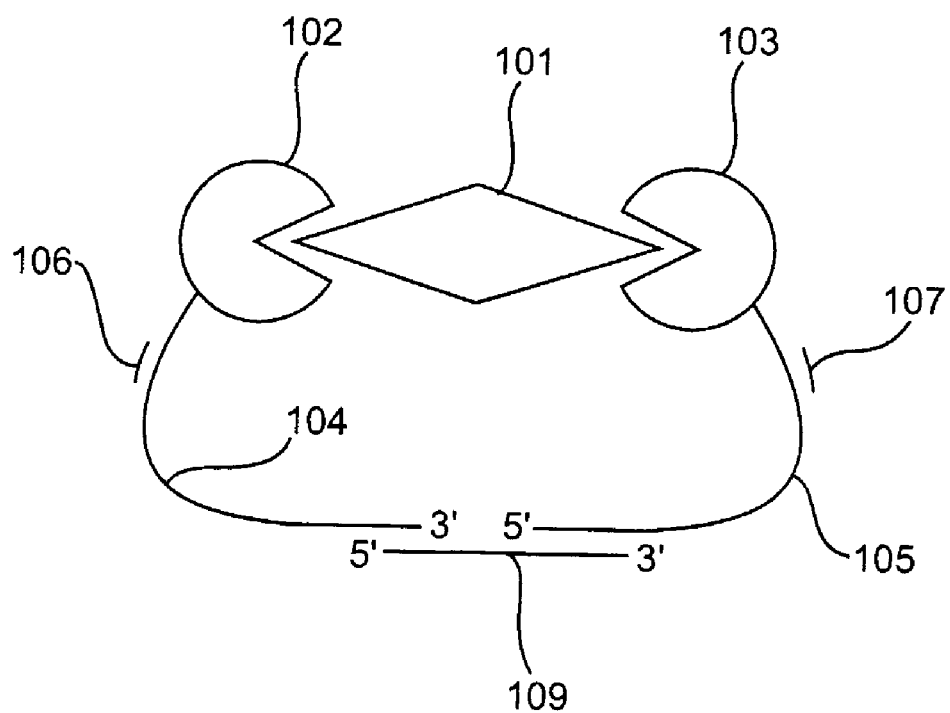

SEQUENCE LISTING

<160> NUMBER OF SEQ ID NOS: 10

<210> SEQ ID NO 1
<211> LENGTH: 32
<212> TYPE: DNA
<213> ORGANISM: Artificial Sequence
<220> FEATURE:
<223> OTHER INFORMATION: Synthetic probe

```
<220> FEATURE:
<221> NAME/KEY: misc_difference
<222> LOCATION: 1
<223> OTHER INFORMATION: 5'-terminal c18-c18-c18-c18-teg-Biotin

<400> SEQUENCE: 1
catcgccctt ggactagcat atctaaatcg tg                                     32

<210> SEQ ID NO 2
<211> LENGTH: 33
<212> TYPE: DNA
<213> ORGANISM: Artificial Sequence
<220> FEATURE:
<223> OTHER INFORMATION: Synthetic probe
<220> FEATURE:
<221> NAME/KEY: misc_difference
<222> LOCATION: 33
<223> OTHER INFORMATION: 3'-terminal c18-c18-c18-c18-teg-biotin

<400> SEQUENCE: 2
tcgtgtctaa tatcgttacc ttgattcccg tcc                                    33

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 3
tacttagaca cgacacgatt tagttt                                            26

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 4
ggtaacgaua uuagacacga cacgauuuag auaugcuagt                             40

<210> SEQ ID NO 5
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 5
attgguaacg auauuagaca cgacacgauu uagtat                                 36

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 6
tatuuagaca cgacacgauu uagauaugcu aguaat                                 36

<210> SEQ ID NO 7
<211> LENGTH: 31
<212> TYPE: DNA
<213> ORGANISM: Artificial Sequence
<220> FEATURE:
<223> OTHER INFORMATION: Synthetic oligonucleotide
```

```
<400> SEQUENCE: 7
attcgauauu agacacgaca cgauuuagta t                              31

<210> SEQ ID NO 8
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 8
tatuuagaca cgacacgauu uagauaugaa t                              31

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
catcgccctt ggactagcat                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
cctcgggaat caaggtaacg                                           20
```

METHODS AND COMPOSITIONS FOR USE IN ANALYTE DETECTION USING PROXIMITY PROBES

CROSS-REFERENCE TO RELATED APPLICATIONS

Pursuant to 35 U.S.C. §119(e), this application claims priority to the filing date of the U.S. Provisional Patent Application Ser. No. 60/579,901 filed Jun. 14, 2004; the disclosure of which is herein incorporated by reference.

ACKNOWLEDGMENT OF GOVERNMENT SUPPORT

This invention was made with Government support under Grant Nos. CA HG00205 awarded by the National Institute of Health. The Government has certain rights in this invention.

INTRODUCTION

1. Background of the Invention

Proximity probing (also termed proximity ligation) is an analyte detection technique capable of detecting the nearness of the two so-called "proximity probes" and is used for specific, sensitive and rapid detection of analytes in a sample. Representative proximity probe assays are described in U.S. Pat. No. 6,511,809; WO 01/61037; WO 03/044231 and Fredriksson et al., (2002) Nature Biotechnology, 20:473-477.

In representative embodiments of such assays, proximity probes that include a binding moiety (with specific affinity for the target molecule) coupled to a reactive nucleic acid are employed. The probes usually work in pairs, each with a coupled nucleic acid capable of interacting with the other one (usually through ligation) when these are in proximity of each other. These nucleic acids are sometimes referred to as reactive nucleic acids. The proximity between the probes is provided when two probes bind their respective binding sites on a target analyte. This proximity enables the two nucleic acids coupled to the probes to interact with one another and give rise to a new nucleic acid sequence, which is then detected and quantified, e.g., by amplification.

While proximity probe based assays reported to date provide useful tools for analyte detection, there is a continued interest in the improvement of such assays. Of particular interest is the development of proximity probe based assays having a sensitivity that is greater than that currently achievable.

2. Relevant Literature

U.S. patents of interest include: U.S. Pat. Nos. 6,558,928; 6,511,809; 5,635,602; and 5,849,878. Published patent applications of interest include: 20020064779 and WO01/61037; WO03/044231; and WO9700446. Also of interest is: Fredriksson et al., (2002) Nature Biotechnology, 20:473-477 Gullberg, et al., Curr Opin Biotechnol. (2003)14(1):82-6; and Gullberg et al., Proc Natl Acad Sci USA. (e publication May 21, 2004).

SUMMARY OF THE INVENTION

Methods and compositions for detecting an analyte in a sample are provided. In practicing the subject methods, a sample is first combined with at least two proximity probes that each include an analyte binding domain and a nucleic acid domain. The resultant mixture is then contacted with at least a pair of asymmetric nucleic acid connectors. Connector mediated proximity dependent interaction between the proximity probes is then detected to determine the presence of the analyte in the sample. Also provided are kits and systems for practicing the subject methods.

FEATURES OF THE INVENTION

One feature of the invention provides method for detecting an analyte in a sample, by producing a mixture by combining the sample and at least one set of at least first and second proximity probes each including an analyte binding domain and a nucleic acid binding domain, wherein the first and second proximity probes can simultaneously bind to the analyte; combining the mixture with first and second asymmetric connectors corresponding to the first and second proximity probes; and then detecting a connector mediated proximity dependent interaction between the first and second proximity probes in order to detect the presence of the analyte in the sample. In some embodiments, the first and second connectors each include regions of complementarity of differing length for both nucleic acid domains of the first and second proximity probes. In some embodiments, such mixture may also include single strand binding protein. In some embodiments, the mixture is subjected to nucleic acid ligation conditions. In certain embodiments, the effective volume of the incubation mixture is reduced, e.g., by including a volume excluder and/or removing water from the mixture.

In such methods of the invention, detection of proximity dependant interaction may be by polymerase chain reaction (PCR) protocol. In some embodiments the proximity dependant interaction is a ligation event between the nucleic acid binding domain of first and second proximity probes.

In such methods, the analyte binding domain of the proximity probes may be an antibody or binding fragment thereof. In such methods of the invention, the detection of proximity dependent interaction may be qualitative or quantitative.

In some embodiments, the subject method employs a single set of proximity probes. In other embodiments, the subject method employs two or more sets of proximity probes.

In such methods of the invention, the first asymmetric connector includes a first region of complementarity for the nucleic acid binding domain of the first proximity probe and a region of complementarity for the nucleic acid binding domain of the second proximity probe, wherein the first region is longer that the second region. In some embodiments, the first region of the first asymmetric connector is at least about 5 nucleotides longer than the second region. In other embodiments, the first region of the first asymmetric connector is from about 13 to 17 nucleotides in length and the second region is from about 8 to 12 nucleotides in length.

In such methods of the invention, the second asymmetric connector includes a first region of complementarity for the nucleic acid binding domain of the second proximity probe and a second region of complementarity for the nucleic acid binding domain of the first proximity probe, wherein the first region is longer than the second region. In some embodiments, the first region of the second asymmetric connector is at least about 5 nucleotides longer that the second region. In other embodiments, the first region of the second asymmetric connector is from about 13 to 17 nucleotides in length and the second region is from about 8 to 12 nucleotides in length.

In such methods of the invention, the analyte may include a single molecule, or the analyte may include two or more non-covalently bound molecules. In some embodiments, the analyte is a peptide. In other embodiments, the analyte is a prion.

In such methods of the invention, the proximity probes may bind to the analyte indirectly, or the proximity probes may bind to the analyte directly.

Another feature of the invention provides kits for detecting and quantifying an analyte in a sample, including at least one set of proximity probes including at least a first and second proximity probes each including an analyte binding domain and a nucleic acid binding domain, and first and second asymmetric connectors corresponding to the first and second proximity probes. The kits may also include a ligase, first and second supplementary nucleic acids, single strand binding proteins, and PCR amplification reagents.

In such kits of the invention, the analyte binding domain is an antibody or binding fragment thereof.

In some embodiments, the subject kits include a single set of proximity probes. In other embodiments, the subject kits include two or more sets of proximity probes.

In such kits of the invention, the first asymmetric connector includes a first region of complementarity for the nucleic acid binding domain of the first proximity probe and a second region of complementarity for the nucleic acid binding domain of the second proximity probe, wherein the first region is longer than said second region. In some embodiments, the first region of the first asymmetric connector is at least about 5 nucleotides longer than the second region. In other embodiments, the first region of the first asymmetric connector is from about 13 to 17 nucleotides in length and the second region is from about 8 to 12 nucleotides in length.

In such kits of the invention, the second asymmetric connector includes a first region of complementarity for the nucleic acid binding domain of the second proximity probe and a second region of complementarity for the nucleic acid binding domain of the first proximity probe, wherein the first region is longer than said second region. In some embodiments, the first region of the second asymmetric connector is at least about 5 nucleotides longer that the second region. In other embodiments, the first region of the second asymmetric connector is from about 13 to 17 nucleotides in length and the second region is from about 8 to 12 nucleotides in length.

Yet another feature of the invention provides a system, which includes at least one set of at least first and second proximity probes each including an analyte binding domain and a nucleic acid binding domains, wherein the first and second proximity probes can simultaneously bind to the analyte; first and second asymmetric connectors corresponding to the first and second proximity probes; and a nucleic acid ligase. Such systems of the invention may also include single strand binding protein, PCR amplification reagents, and first and second supplementary nucleic acids.

In such systems of the invention, the analyte binding domain is an antibody or binding fragment thereof.

In some embodiments, the subject system includes a single set of proximity probes. In other embodiments, the subject system includes two or more sets of proximity probes.

In such systems of the invention, the first asymmetric connector includes a first region of complementarity for the nucleic acid binding domain of the first proximity probe and a second region of complementarity for the nucleic acid binding domain of the second proximity probe, wherein the first region is longer than said second region. In some embodiments, the first region of the first asymmetric connector is at least about 5 nucleotides longer than the second region. In other embodiments, the first region of the first asymmetric connector is from about 13 to 17 nucleotides in length and the second region is from about 8 to 12 nucleotides in length.

In such systems of the invention, the second asymmetric connector includes a first region of complementarity for the nucleic acid binding domain of the second proximity probe and a second region of complementarity for the nucleic acid binding domain of the first proximity probe, wherein the first region is longer than said second region. In some embodiments, the first region of the second asymmetric connector is at least about 5 nucleotides longer that the second region. In other embodiments, the first region of the second asymmetric connector is from about 13 to 17 nucleotides in length and the second region is from about 8 to 12 nucleotides in length.

BRIEF DESCRIPTION OF THE DRAWINGS

With respect to the figures, it is noted that, according to common practice, the various features of the drawings may not be not to-scale. On the contrary, the dimensions of the various features may be arbitrarily expanded or reduced for clarity. Included in the drawings are the following figures:

FIG. 1 shows a schematic representation of the interaction of two proximity probes, which proximity probes include analyte binding domains (102 and 103) and nucleic acid binding domains (104 and 105), with an analyte (101). The top panel shows a schematic of a proximity dependant interaction, which includes a first form of the asymmetric nucleic acid connector (108). The bottom panel shows a schematic of a proximity dependant interaction, which includes a second form of the asymmetric nucleic acid connector (109). Forward (107) and reverse (106) primers complementary to the nucleic acid binding domains (105 and 104) for detection of proximity dependent interaction between the first and second proximity probes are also shown.

DEFINITIONS

Figure 2:
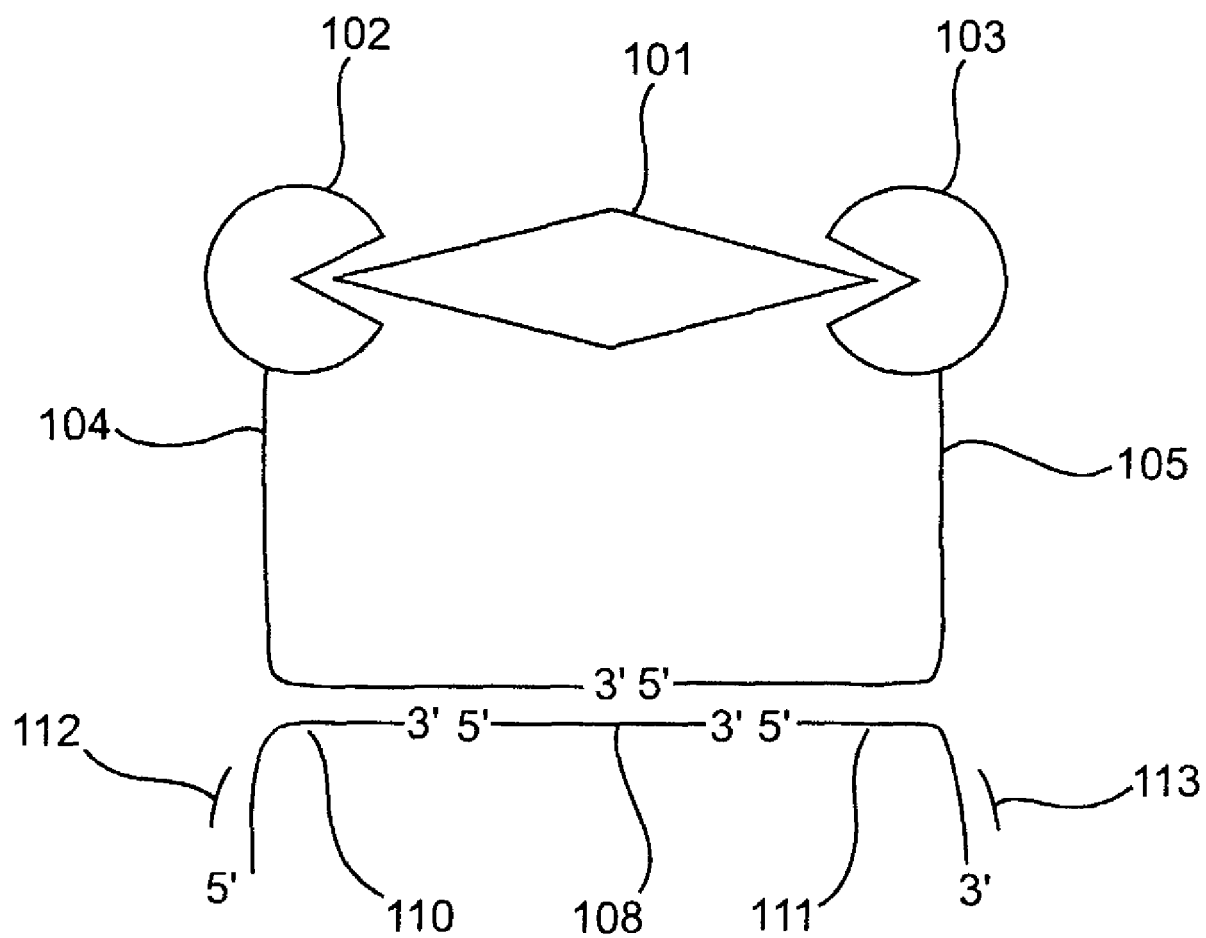
FIG. 2 shows a schematic representation of the interaction of two proximity probes, which proximity probes include analyte binding domains (102 and 103) and nucleic acid binding domains (104 and 105), with an analyte (101) and two supplementary nucleic acids (110 and 111). Forward (113) and reverse (112) primers complementary to the supplementary nucleic acids (111 and 110) for detection of proximity dependent interaction between the first and second proximity probes are also shown.

The term "analyte" refers to a substance to be detected or assayed by the method of the present invention. Typical analytes may include, but are not limited to peptides, proteins, nucleic acids, small molecules, including organic and inorganic molecules, viruses and other microorganisms, cells etc., as well as fragments and products thereof, such that any analyte can be any substance or entity that can participate in a specific binding pair interaction, e.g., for which attachment sites, binding members or receptors (such as antibodies) can be developed.

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. The terms also include such molecules with modifications, such as by methylation and/or by capping, and unmodified forms of a polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. Nucleotides can be referred to throughout using lower or upper case letters.

The terms "deoxyribonucleic acid" and "DNA" as used herein mean a polymer composed of deoxyribonucleotides.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences.

An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

By "selectively bind" is meant that the molecule binds preferentially to the target of interest or binds with greater affinity to the target than to other molecules. For example, a DNA molecule will bind to a substantially complementary sequence and not to unrelated sequences.

The term "amplification" refers to the process in which "replication" is repeated in cyclic process such that the number of copies of the nucleic acid sequence is increased in either a linear or logarithmic fashion. Such replication processes may include but are not limited to, for example, Polymerase Chain Reaction (PCR).

The term "ligase" refers to an enzyme that catalyzes the formation of a phosphodiester bond between adjacent 3' hydroxyl and 5' phosphoryl termini of oligonucleotides that are hydrogen bonded to a complementary strand and the reaction is termed "ligation."

The term "ligation" refers to joining of 3' and 5' ends of two proximal positioned antibody bound DNA labels by the enzyme ligase in the presence of a connector.

As used herein, a "biological sample" refers to a sample of tissue or fluid isolated from a subject, which in the context of the invention generally refers to samples suspected of containing nucleic acid and/or viral particles of human rhinovirus, which samples, after optional processing, can be analyzed in an in vitro assay. Typical samples of interest include, but are not necessarily limited to, respiratory secretions (e.g., samples obtained from fluids or tissue of nasal passages, lung, and the like), blood, plasma, serum, blood cells, fecal matter, urine, tears, saliva, milk, organs, biopsies, and secretions of the intestinal and respiratory tracts. Samples also include samples of in vitro cell culture constituents including but not limited to conditioned media resulting from the growth of cells and tissues in culture medium, e.g., recombinant cells, and cell components.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

Methods and compositions for detecting an analyte in a sample by proximity dependant interaction are provided. In practicing the subject methods, a sample is first combined with at least two proximity probes, which proximity probes each include an analyte binding domain and a nucleic acid domain. The resultant mixture is then contacted with at least a pair of of asymmetric connectors. Connector mediated proximity dependent interaction between the proximity probes is then detected to determine the presence of the analyte in the sample. Also provides are kits and systems for practicing the subject methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The practice of the present invention will employ, unless otherwise indicated, conventional methods of chemistry, biochemistry, recombinant DNA techniques and virology, within the skill of the art. Such techniques are explained fully in the literature. See, e.g., Fundamental Virology, 2nd Edition, vol. I & II (B. N. Fields and D. M. Knipe, eds.); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Oligonucleotide Synthesis (N. Gait, ed., 1984); A Practical Guide to Molecular Cloning (1984).

As summarized above, the subject invention provides methods and compositions for proximity-probe based detection of an analyte in a sample. In further describing the subject invention, the methods are reviewed first in greater detail, followed by a discussion of representative applications in which the methods find use, as well as a review of representative kits and systems that find use in practicing the subject methods.

Methods

As summarized above, the subject invention provides methods for detecting one or more analytes in a sample. More specifically, the subject methods are proximity probe based assays for detecting one or more analytes in a sample.

A feature of the subject methods is that they provide for significantly increased sensitivity as compared to the proximity probe based protocol reported in Fredricksson et al., Nature Biotechnology (2002) 20:473-477. By significantly increased sensitivity is meant that the subject methods are least about 2-fold more sensitive, such as at least about 20-fold more sensitive, including at least about 100 fold more sensitive than the assays reported in Fredriksson et al., Nature Biotechnology (2002) 20:473-477. Therefore, the subject methods are sufficiently sensitive to assay for an analyte present in a sample at a concentration of less than about 0.1 pM, such as less than about 10 fM, including less than about 1 fM or lower.

In practicing the subject methods, a sample to be assayed is contacted with a set of proximity probes for each different target analyte of interest. A given set of proximity probes for a given target analyte includes at least two different proximity probes for the target analyte, and may include more than two different probes, e.g., 3, 4, 5 or more probes. At least two of the probes of a given set are able to simultaneously bind to the target analyte. Where a sample is assayed for a single analyte, a single set of proximity probes may be contacted with the sample. Alternatively, where the sample is assayed for two or more different analytes, two or more different sets of probes are contacted with the sample.

The resultant mixture of sample and proximity probes is then contacted with at least a pair of asymmetric nucleic acid connectors or splints. Any resultant asymmetric connector mediated proximity dependent interactions are then detected to determine the presence of the target analyte in the sample.

In further describing the subject methods, the proximity probes and asymmetric connectors employed in the subject methods will be described first in greater detail, followed by a more in depth review of the different steps that make up the subject methods.

Proximity Probes

The proximity probes for use with the methods of the present invention include an analyte binding domain (also referred to herein as an affinity ligand) and a nucleic acid domain (also referred to herein as a nucleic acid tag or tail). As detailed below, the analyte binding domain and the nucleic acid domain are connected, whereby "connected" is meant the two domains of the proximity probe are associated with one another, e.g., by covalent cross-linkage, or non-covalent association (such as streptavidin-biotin coupling).

Accordingly, the subject proximity probes, which may also be viewed as nucleic acid tailed or tagged affinity ligands, are conjugate molecules that include an affinity ligand (i.e., analyte binding domain) conjugated to a tag or tail nucleic acid (i.e. nucleic acid domain), where the two components are generally (though not necessarily) covalently joined to each other, e.g. directly or through a linking group. In other words, in representative embodiments the "tailed" affinity ligand is made up of an affinity ligand covalently joined to a tag nucleic acid, either directly or through a linking group, where the linking group may or may not be cleavable, e.g. enzymatically cleavable (for example, it may include a restriction endonuclease recognized site), photo labile, etc.

In certain embodiments, the affinity ligand (i.e. analyte binding) domain, moiety or component of the nucleic acid tailed affinity ligands or proximity probes is a molecule that has a high binding affinity for a target-analyte. By high binding affinity is meant a binding affinity of at least about $10^{-4}$ M, usually at least about $10^{-6}$ M or higher, e.g., $10^{-9}$ M or higher. The affinity ligand may be any of a variety of different types of molecules, so long as it exhibits the requisite binding affinity for the target protein when present as tagged affinity ligand. In certain embodiments, the affinity ligand is a ligand that has medium or even low affinity for its target analyte, e.g., less than about $10^{-4}$ M.

As such, the affinity ligand may be a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

The small molecule may be any molecule, as well as binding portion or fragment thereof, that is capable of binding with the requisite affinity to the target protein. Generally, the small molecule is a small organic molecule that is capable of binding to the target analyte of interest. The small molecule will include one or more functional groups necessary for structural interaction with the target analyte, e.g., groups necessary for hydrophobic, hydrophilic, electrostatic or even covalent interactions. Where the target analyte is a protein, the drug moiety will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups. As described in greater detail below, the small molecule will also comprise a region that may be modified and/or participate in covalent linkage to the tail component of the tailed affinity ligand, without substantially adversely affecting the small molecule's ability to bind to its target analyte.

Small molecule affinity ligands often comprise cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs.

As such, the small molecule may be obtained from a library of naturally occurring or synthetic molecules, including a library of compounds produced through combinatorial means, i.e. a compound diversity combinatorial library. When obtained from such libraries, the small molecule employed will have demonstrated some desirable affinity for the protein target in a convenient binding affinity assay. Combinatorial libraries, as well as methods for the production and screening, are known in the art and described in: U.S. Pat. Nos. 5,741, 713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

As pointed out, the affinity ligand can also be a large molecule. Of particular interest as large molecule affinity ligands are antibodies, as well as binding fragments and mimetics thereof. Where antibodies are the affinity ligand, they may be derived from polyclonal compositions, such that a heterogeneous population of antibodies differing by specificity are each tagged with the same tag nucleic acid, or monoclonal compositions, in which a homogeneous population of identical antibodies that have the same specificity for the target protein are each tagged with the same tag nucleic acid. As such, the affinity ligand may be either a monoclonal and polyclonal antibody. In yet other embodiments, the affinity ligand is an antibody binding fragment or mimetic, where these fragments and mimetics have the requisite binding affinity for the target protein. For example, antibody fragments, such as Fv, F(ab)$_2$ and Fab may be prepared by cleavage of the intact protein, e.g. by protease or chemical cleavage. Also of interest are recombinantly produced antibody fragments, such as single chain antibodies or scFvs, where such recombinantly produced antibody fragments retain the binding characteristics of the above antibodies. Such recombinantly produced antibody fragments generally include at least the VH and VL domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments and mimetics thereof may be obtained from commercial sources and/or prepared using any convenient technology, where methods of producing polyclonal antibodies, monoclonal antibodies, fragments and mimetics thereof, including recombinant derivatives thereof, are known to those of the skill in the art.

Also suitable for use as binding domains are polynucleic acid aptimers. Polynucleic acid aptamers may be RNA oligonucleotides which may act to selectively bind proteins, much in the same manner as a receptor or antibody (Conrad et al., Methods Enzymol. (1996), 267 (Combinatorial Chemistry), 336-367). In certain embodiments where the affinity ligand is a nucleic acid, e.g., an amptamer, the target analyte is not a nucleic acid. In certain embodiment, the affinity ligand is not a nucleic acid.

Importantly, the affinity ligand will be one that includes a domain or moiety that can be covalently attached to the nucleic acid tail without substantially abolishing the binding affinity for the affinity ligand to its target protein.

Figure 3:
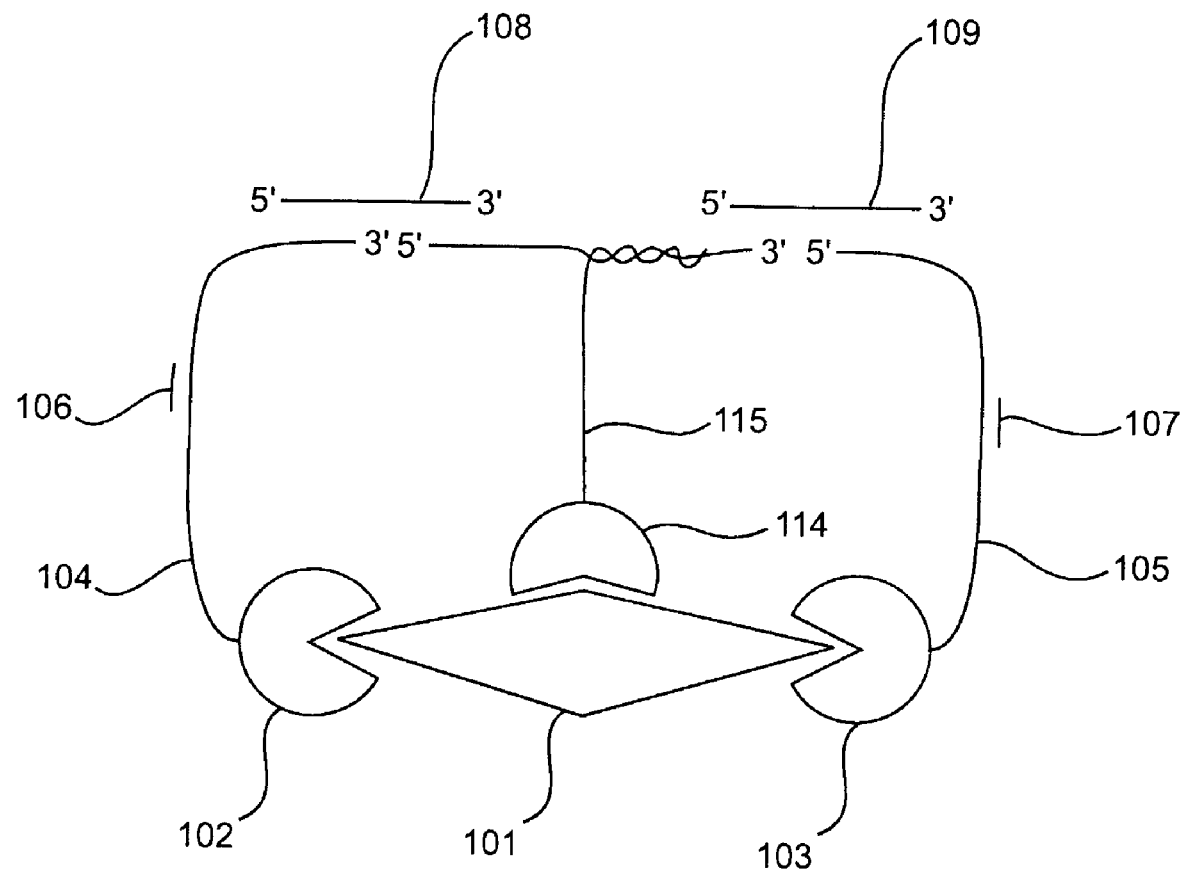
FIG. 3 shows a schematic representation of the interaction of three proximity probes, which proximity probes include analyte binding domains (102, 103, and 114) and nucleic acid binding domains (104, 105, and 115), with an analyte (101) and asymmetric nucleic acid connectors (108 and 109). Forward (107) and reverse (106) primers complementary to the nucleic acid binding domains (105 and 104) for detection of proximity dependent interaction between the first and second proximity probes are also shown.

Turning now to the tail or tag nucleic acid domains of the subject proximity probes, the nucleic acid domains may be a single stranded nucleic acid molecule, a partially double stranded and partially single stranded molecule, or a double stranded molecule that includes of a region that is double stranded and a region where the two nucleic acid strands are not complementary and therefore single stranded. As such, in certain embodiments, the nucleic acid tail is made up of a single stranded nucleic acid, as depicted in FIG. 1. In yet other embodiments, the nucleic acid tail may be made up of two partially complementary nucleic acid strands, as shown in FIG. 3, where the two strands include a hybridized region and non-hybridized region.

The nucleic acid domains are generally of a length sufficient to allow asymmetric connector or splint mediated interaction with the nucleic acid domain of another proximity probe when bound to a target analyte. Nucleic acid domains for use in the subject methods are usually in the range of between about 30 up to about 1000 nucleotides in length, where in certain embodiments they may range from about 30 to about 500 nucleotides in length including from about 30 to about 250 nucleotides in length, e.g., from about 30 to about 160 nucleotides in length, such as from about 20 to about 150 nucleotides in length, from about 22 to about 130 nucleotides in length, from about 24 to about 110 nucleotides in length, from about 26 to about 90 nucleotides in length, from about 28 to about 80 nucleotides in length, from about 30 to about 75 nucleotides in length, from about 32 to about 70 nucleotides in length, from about 34 to about 60 nucleotides in length, and so on, where in certain representative embodiments, the nucleic acid tail or tag domains range in length from about 28 to about 80 nucleotides in length, from about 30 to about 75 nucleotides in length, from about 32 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

As indicated above, the tag may be made up of ribonucleotides and deoxyribonucleotides as well as synthetic nucleotide residues that are capable of participating in Watson-Crick type or analogous base pair interactions.

The sequence of the tag nucleic acid is chosen or selected with respect to their corresponding asymmetric connectors or splints, as described in greater detail below. Once the sequence is identified, the tag nucleic acids may be synthesized using any convenient protocol, where representative protocols for synthesizing nucleic acids are described in greater detail below in terms of the preparation of the tag complement or universal arrays employed in the subject methods.

The two components of the nucleic acid tailed affinity ligand conjugate, i.e. proximity probe, are joined together either directly through a bond or indirectly through a linking group. Where linking groups are employed, such groups are chosen to provide for covalent attachment of the tail and affinity ligand moieties through the linking group, as well as maintain the desired binding affinity of the affinity ligand for its target analyte. Linking groups of interest may vary widely depending on the affinity ligand moiety. The linking group, when present, is in many embodiments biologically inert. A variety of linking groups are known to those of skill in the art and find use in the subject conjugates. In representative embodiments, the linking group is generally at least about 50 daltons, usually at least about 100 daltons and may be as large as 1000 daltons or larger, but generally will not exceed about 500 daltons and usually will not exceed about 300 daltons. Generally, such linkers will comprise a spacer group terminated at either end with a reactive functionality capable of covalently bonding to the drug or ligand moieties. Spacer groups of interest possibly include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject tagged affinity ligands include heterofunctional compounds, such as azidobenzoyl hydrazide, N-[4-(p-azidosalicylamino) butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The above-described tailed target affinity ligands or proximity probes employed in the subject methods may be prepared using any convenient protocol. In representative embodiments, tag nucleic acids will be conjugated to the affinity ligand, either directly or through a linking group. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the tagged affinity ligand include: hydroxy, sulfhydryl, amino, and the like. The particular portion of the different components that are modified to provide for covalent linkage will be chosen so as not to substantially adversely interfere with that components desired binding affinity for the target protein. Where necessary and/or desired, certain moieties on the components may be protected using blocking groups, as is known in the art, see, e.g. Green & Wuts, Protective Groups in Organic Synthesis (John Wiley & Sons) (1991). Methods for producing nucleic acid antibody conjugates are well known to those of skill in the art. See e.g. U.S. Pat. No. 5,733,523, the disclosure of which is herein incorporated by reference.

In other embodiments, tailed affinity ligands can be produced using in vitro protocols that yield nucleic acid-protein conjugates, i.e., molecules having nucleic acids, e.g., coding sequences, covalently bonded to a protein, i.e., where the affinity ligand is produced in vitro from vectors which encode the tagged affinity ligands. Examples of such in vitro protocols of interest include: RepA based protocols (See e.g., Fitzgerald, DDT (2000) 5:253-258 and WO 98/37186), ribosome display based protocols (se e.g., Hanes et al., Proc. Nat'l Acad. Sci. USA (1997) 94:4937-42; Roberts, Curr Opin Chem Biol 1999 June; 3(3):268-73; Schaffitzel et al., J Immunol Methods 1999 Dec. 10; 231(1-2):119-35; and WO 98/54312), etc.

Asymmetric Nucleic Acid Connectors

As summarized above, a feature of the subject methods is the use of at least one pair of asymmetric connectors or splints. In certain embodiments, the subject methods use a single pair of connectors for each given pair of proximity probes employed in a given assay. As such, where only two proximity probes are employed in a given assay, i.e., the assay employs a single set of proximity probes where the set includes only two proximity probes, the assay will employ a single pair of asymmetric connectors. Alternatively, where the assay employs two pairs of proximity probes, e.g., two sets for two different target analytes, the assay will employ two pairs of asymmetric connectors, one for each pair. In yet other embodiments where a given set is made up of three or more different proximity probes, a pair of asymmetric connectors is employed for any given two tails found in the set. For example, in the embodiment shown in FIG. 3, while a set is employed that includes three different proximity probes, the set effectively includes two distinct pairs of nucleic acid tails, and therefore is employed with two pairs of asymmetric probes, one pair for each nucleic acid tail pair. In yet other embodiments, a single pair of connectors may be used for two or more different pairs of probes (or at least tails) where sequence variations between any such tail pairs allow for the use of a single pair of connectors. For example, one can employ to pairs of tails whose sequence is chosen such that the assymetric connectors bind differently depending on the pair with which they are hybridized. As such, in a representative embodiment, one can use the same connector set for each probe (or at least tail) pair but just offset the ligation site on the connectors in order to remove crossreactions in between sets, such that one set ligates at 10+15 or 15+10 while the next set ligates at 9+16 or 16+9, etc.

A given asymmetric connector is able to hybridize or bind simultaneously to two different nucleic acid tails. Thus, a given asymmetric connector corresponds to two different nucleic acid tails, such that it has regions of complementarity for two different nucleic acid tails. A feature of the asymmetric connectors is that they preferentially bind to a first nucleic acid tail as opposed to a second, i.e. a first member of a corresponding pair as opposed to a second member of a corresponding pair. In other words, an asymmetric connector will selectively hybridize to a first member of its corresponding pair of nucleic acid tails as opposed to a second member. This feature of selective hybridization found in the asymmetric connectors may be achieved using any convenient way. For example, non-natural nucleic acid of increased hybridization strength, such as locked nucleic acid or peptide nucleic acids may be employed in the region that preferentially binds to a nucleic acid tail. Alternatively, mismatches or secondary structures, e.g., hairpins, may be introduced in a region of the connectors to achieve the desired asymmetric binding efficiency to a corresponding pair of nucleic acid tails. In representative embodiments, the asymmetric binding characteristics of the connectors are achieved by having regions of complementarity of differing length, as described in greater detail below.

As noted above, a feature of the invention is that at least one pair of asymmetric connectors is employed. A given pair is made up of individual asymmetric connectors of substantially opposite binding characteristics with respect to their corresponding nucleic acid tail pairs. As such, while a given asymmetric connector pair each corresponds, i.e., hybridizes to, the same pair of nucleic acid tails, the members of the pair have opposing hybridization specificity for the corresponding nucleic acid tail pair, such that a first connector preferentially hybridizes to a first tail of the pair, and a second connector preferentially hybridizes to a second tail of the pair.

As indicated above, each member of a given pair of asymmetric nucleic acid connectors each includes two regions of complementarity, where in certain representative embodiments, the number of nucleotides of the first region is not equal to the number of nucleotides of the second region. That is, the asymmetric nucleic acid connectors have a first region of complementarity that is longer than the second region of complementarity. In these embodiments, in a given pair the longer region of complementarity (e.g., 3' end or 5' end) of a first asymmetric nucleic acid connector of the pair hybridizes to the same nucleic acid tail to which the shorter region of complementarity of the second nucleic acid connector of the pair binds. Likewise, the shorter region of complementarity (e.g., 3' end or 5' end) of the first asymmetric nucleic acid connector of a given pair binds to the same nucleic acid tail as the longer region of complementarity of the second nucleic acid connector of the pair.

The asymmetric nucleic acid connectors are able to simultaneously anneal to both nucleic acid domains or tails of a given pair of proximity probes, where such simultaneous binding produces a stable duplexed structure that contains all three nucleic acids. Such a duplexed structure brings together the 3' hydroxyl free end of the nucleic acid domain of the first proximity probe and the 5' phosphoryl free end of the nucleic acid domain of the second proximity probe of a given pair.

The asymmetric nucleic acids are generally of a length sufficient to provide for the above described simultaneous binding of nucleic acid tails of a pair of proximity probes. In representative embodiments, the asymmetric connectors range in length from about 15 to about 50 nucleotides, including from about 20 to about 40 nucleotides, e.g., from about 25 to about 30 nucleotides.

In representative embodiments, for a given pair of asymmetric connectors, the first asymmetric connector includes a first 3' region of complementarity for the nucleic acid domain of the 5' free proximity probe and a second 5' region of complementarity for the nucleic acid domain of the 3' free proximity probe, wherein the first region is longer that the second region. The first region of the first population of asymmetric connector is at least about 3-12 nucleotides longer than the second region, such as from about 4-11, 5-10, 6-9, 7-8 nucleotides longer than the second region. In some embodiments, the first region of the first population of asymmetric connector is about 4, 5, 6, 7, 8, or 9 nucleotides longer than the second region. In other embodiments, the first region of the first asymmetric connector is from about 13 to 17, 12 to 16, 11 to 15, or 12 to 14 nucleotides in length and the second region is from about 6 to 12, 7 to 11, or 8 to 10 nucleotides in length.

With respect to the second asymmetric connector of these embodiments, the second asymmetric connector includes a first 5' region of complementarity for the nucleic acid domain of the 3' free proximity probe and a second 3' region of complementarity for the nucleic acid domain of the 5' free proximity probe, wherein the first region is longer that the second region. The first region of the second population of asymmetric connector is at least about 3-12 nucleotides longer than the second region, such as from about 4-11, 5-10, 6-9, 7-8 nucleotides longer than the second region. In some embodiments, the first region of the second population of asymmetric connector is 4, 5, 6, 7, 8, or 9 nucleotides longer than the second region. In other embodiments, the first region of the second asymmetric connector is from about 13 to 17, 12 to 16, 11 to 15, or 12 to 14 nucleotides in length and the second region is from about 6 to 12, 7 to 11, or 8 to 10 nucleotides in length.

In some embodiments, the asymmetric nucleic acid connectors may contain the nucleotide uracil in the place of thymine. In such embodiments, the nucleotide uracil is used to enable the degradation of the asymmetric connectors prior to amplification so that the connectors cannot hybridize during the amplification process. In such embodiments, the asymmetric connectors are generally at least about 30 nucleotides in length, such as at least about 50 nucleotides in length.

In other embodiments, the asymmetric nucleic acid connectors for use in the subject methods may further include mismatched (i.e., non-complementary) nucleotides at each of the 3' and 5' ends in order to reduce the probability of the connectors as acting as primers during amplification. In some embodiments, the number of mismatched nucleotides is from about 1 to 8, 2 to 7, 3 to 6, 4 to 5 nucleotides in length, more usually, the number of mismatched nucleotides is 2, 3, 4, 5, or 6 nucleotides in length.

Method Steps

As summarized above, in practicing the subject methods, the sample is first combined with at least one set (made up of a least two different) proximity probes. The resultant mixture is then contacted with a least one pair of asymmetric connectors (e.g., a pair for any given two nucleic acid tails) and any resultant connector mediated proximity dependent interactions between the tails of a given pair proximity probes is detected. Each of these steps of the subject methods is now reviewed in greater detail.

As indicated above, in practicing the subject methods a sample is combined with at least one set of proximity probes, where a given set of proximity probes may be made up of two or more different proximity probes. As such, in certain embodiments where a sample is contacted with a single set made up of two proximity probes, the set will include two different populations of proximity probes. A first population of proximity probes will have the single stranded nucleic acid domain coupled to the analyte binding domain by the 5' end of the nucleic acid molecule, wherein such proximity probes will include a single stranded nucleic acid binding domain having a free 3' hydroxyl end. A second population of proximity probes will have the single stranded nucleic acid domain coupled to the analyte binding domain by the 3' end of the nucleic acid molecule, wherein such proximity probes will include a single stranded nucleic acid binding domain having a free 5' phosphate end.

In yet other representative embodiments where the set is made up of three distinct proximity probes, the employed set will include three or more different populations of proximity probes. A first population of proximity probes will have the single stranded nucleic acid domain coupled to the analyte binding domain by the 5' end of the nucleic acid molecule, wherein such proximity probes will include a single stranded nucleic acid domain having a free 3' hydroxyl end. A second population of proximity probes will have the single stranded nucleic acid binding coupled to the analyte binding domain by the 3' end of the nucleic acid molecule, wherein such proximity probes will include a single stranded nucleic acid domain having a free 5' phosphate end. A third population of proximity probes will have a nucleic acid domain that is a single stranded molecule that is coupled to the analyte binding domain by the 3' end of the nucleic acid, wherein such proximity probes will include a free 5' and. Such a third population of proximity probes will also have a second single strand nucleic acid molecule that associates with the coupled nucleic acid molecule, wherein the associated molecule has a region of complementarity to the 5' end of the coupled nucleic acid molecule, such that the associated molecule hybridizes to the coupled molecule forming a double stranded region and two single strand regions forming a free 5' phosphate end and a free 3' hydroxyl end.

As indicated above, in certain embodiments a sample is assayed for two or more different target analytes. In such embodiments, the sample is contacted with a set of proximity probes for each target analytes, such that the number of sets contacted with the sample may be two or more, e.g., three or more, four or more etc., where such methods find particular use in multiplex and high-throughput applications.

In representative embodiments, the amount of proximity probes that is added to a sample provides or a sufficiently low concentration of proximity probe in the product mixture to ensure that the proximity probes will not randomly come into close proximity with one another in the absence of binding to a target analyte, at least not to any great or substantial degree. As such, only when two or more of the proximity probes bind the analyte through the binding interaction between the binding domains of the proximity probes and the binding sites of the analyte, the proximity probes come into close proximity to one another. In representative embodiments, the concentration of the proximity probes in the product mixture following combination with the sample ranges from about 1 fM to 1 μM, such as from about 1 pM to about 1 nM, including from about 1 pM to about 100 nM.

Following combination of the sample and set(s) of proximity probes, the product mixture may be incubated for a period of time sufficient for the proximity probes to bind target analyte, if present, in the sample. In representative embodiments, the product mixture is incubated for a period of time ranging from about 5 min to about 5 hours, including from about 30 min to about 2 hours, at a temperature ranging from about 10 to about 50° C., including from about 20 to about 37° C. Conditions under which the reaction mixture is maintained under the step may be stringent conditions, as defined above.

In certain embodiments, the effective volume of the incubation mixture is reduced, at least during the portion of the incubation step in which the proximity probes are binding to target analyte, if present in the sample. In these embodiments, the effective volume of the incubation mixture may be reduced for a number of different reasons. In certain embodiments, the effective volume of the incubation mixture is reduced in order to allow for the use of medium and low affinity ligands and/or increase the sensitivity of the assay. For example, in certain embodiments where the effective volume of the incubation mixture is reduced, the affinity ligands may be medium or low affinity binders, by which is meant that the affinity ligands may have a binding affinity for their target analyte that is less than about $10^{-4}$ M, such as about 1 nM Kd. In certain embodiments, the sensitivity of the assay may be increased such that the assay can detect as few as about 100 or fewer target analytes in a 1 μl sample, including as few as about 75 or fewer target analytes in a 1 μl sample, including as few as about 50 or fewer target analytes in a 1 μl sample.

In certain embodiments, a "crowding agent" or "volume excluder" is included in the mixture during the incubation step reviewed above, e.g., to reduce the effective volume of the incubation mixture during binding of the proximity probes to their target analyte. Typically, the "crowding agent" is a water soluble macromolecular material. Suitable macromolecular materials broadly comprise biocompatible natural or synthetic polymers having an average molecular weight of from about 1500 to several million, which do not specifically interact with the other reagents in the mixture, or the product. Such polymers are known in the art as "volume-excluders", as their primary function is to occupy volume in the in vitro reaction medium and provide a highly concentrated environment for biochemical reactions, e.g., approximating in vivo conditions. The volume-excluding polymers must of course be sufficiently soluble to provide the required concentration. Suitable exemplary polymers include, but are not limited to: commercially available polyethylene glycol (PEG) polymers, e.g., having an average molecular weight greater than about 2000, FICOLL polymers such as those having an average molecular weight of about 70,000, bovine plasma albumin, glycogen, polyvinylpyrrolidone, dextran, etc. PEG polymers of higher molecular weights, especially, PEG 1450, PEG 3350, PEG 6000 (also sold as PEG 8000), and PEG 20,000, having average molecular weights of about 1450, 3000-3700, 6000-7500, and 15,000-20,000, respectively, are employed in representative embodiments. PEG 6000 and PEG 8000 are employed in representative embodiments. The concentration of the volume-excluding polymers in the incubation reaction in representative embodiments falls within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

In those embodiments where a volume excluder is employed, prior to the next step of the subject methods, reviewed below, the incubation mixture may be diluted to account for the presence of the volume excluder, e.g., by at least about 2-fold or more, such as at least about 5-fold or more, including at least about 10-fold or more, depending on the amount of volume excluder that is present, the nature of the dilution fluid, etc., where in representative embodiments the dilution fluid is water or some other suitable aqueous fluid of water and one or more solutes, e.g., salts, buffering agents, etc.

Instead of, or in addition to, the use of a volume excluder, the incubation mixture may be reduced in volume during incubation by removing a portion of the water from incubation mixture, e.g., via evaporation. In these embodiments, the volume of the fluid may be reduced by at least about 2-fold or more, such as at least about 5-fold or more, including at least about 10-fold or more, as desired. Importantly, not all of the water is removed from the incubation mixture in these embodiments. Any convenient protocol may be employed for reducing the volume of the incubation mixture by removing a select portion of the water therefrom. An instrument for controlling evaporation rate by monitoring and adjusting humidity and temperature may be employed, where in certain embodiments the volume of the incubation mixture is monitored, e.g., by continuously measuring the volume of the incubation mixture, where when appropriately evaporated, the ligation and PCR-mixes may be added, as described above. As desired, a heating block could be used to enhance the evaporation. Alternatively, the volume of the incubation mixture may be reduced by filtrating out water. In representative embodiments, a size exclusion filter is used to selectively contain molecules of sizes larger than a cut off limit while smaller molecules and water is removed by passage through the filter. The force placed on the solution to move it trough the filter may be by either centrifugation or vacuum suction.

Following the interaction of the proximity probes and analyte, two populations of asymmetric nucleic acid connectors (108 and 109) are added to the mixture (which may or may not have been diluted, as reviewed above (FIG. 1). As described above, the two populations of asymmetric nucleic acid connectors have two regions of complementarity, wherein one region of complementarity is longer than the other. Upon binding of the binding domains (102 and 103) of the proximity probes to the analyte (101), the two nucleic acid domains (104 and 107) of the two populations of proximity probes come into close proximity to one another. As a result, the two populations of asymmetric nucleic acid connectors (108 and 109) are capable of binding the proximity probes bound to the target analyte.

As indicated above, in certain embodiments, three or more populations of proximity probes that are specific for three or more different binding domains of an analyte are used (FIG. 3). In such embodiments, a third population of proximity probe is used that includes an binding domain (114) and nucleic acid domain (115), wherein the nucleic acid domain is a single stranded molecule that is coupled to the analyte binding domain by the 3' end of the nucleic acid, wherein such proximity probes will include a free 5' and. Such a third population of proximity probes will also have a second single strand nucleic acid molecule that associates with the coupled nucleic acid molecule, wherein the associated molecule has a region of complementarity to the 5' end of the coupled nucleic acid molecule, such that the associated molecule hybridizes to the coupled molecule forming a double stranded region and two single strand regions forming a free 5' phosphate end and a free 3' hydroxyl end.

The amount of asymmetric connectors that is contacted with the reaction mixture may vary, where in certain embodiments the amount that is added is sufficient to produce a product composition in which the asymmetric connectors are present at a concentration ranging from about 1 pM to about 1 mM, such as from about 1 nM to about 100 µM, including from about 100 nM to about 1 µM.

Following combination with the assymetric connectors, the product mixture may be incubated for a period of time sufficient for the asymmetric connectors to bind proximate nucleic acid tails, if present. In representative embodiments, the product mixture is incubated for a period of time ranging from about 5 min to about 5 hours, including from about 30 min to about 2 hr, at a temperature ranging from about 10 to about 50° C., including from about 20 to about 37° C. Following combination of the sample/proximity probe mixture with the asymmetric connectors as described above, the product composition is then assayed for the presence of any connector mediated proximity dependent interactions. In general, any convenient protocol that is capable of detecting the presence of proximity depending interactions may be employed. The detection protocol may or may not require a separation step, where in certain embodiments the detection protocol does not require a detection step.

In one representative embodiment, the connector mediated proximity dependent interaction of the proximity probes is detected by a protocol that includes nucleic acid ligation of the free 3' hydroxyl and 5' phosphate ends of the nucleic acid domains of the proximity probes, and subsequent detection of the ligated product. In these representative embodiments, ligation of the connector stabilized nucleic acid domains of the proximity probes is achieved by contacting the reaction mixture with a nucleic acid ligating activity, e.g., provided by a suitable nucleic acid ligase, and maintaining the product thereof under conditions sufficient for ligation of the nucleic acid tails to occur.

In many embodiments of the subject invention, the proximal proximity probe nucleic acid domains are ligated to each other in this ligation step by using a ligase. As is known in the art, ligases catalyze the formation of a phosphodiester bond between juxtaposed 3'-hydroxyl and 5'-phosphate termini of two immediately adjacent nucleic acids when they are annealed or hybridized to a third nucleic acid sequence to which they are complementary. Any convenient ligase may be employed, where representative ligases of interest include, but are not limited to: Temperature sensitive and thermostable ligases. Temperature sensitive ligases, include, but are not limited to, bacteriophage T4 DNA ligase, bacteriophage T7 ligase, and E. coli ligase. Thermostable ligases include, but are not limited to, Taq ligase, Tth ligase, and Pfu ligase. Thermostable ligase may be obtained from thermophilic or hyperthermophilic organisms, including but not limited to, prokaryotic, eucaryotic, or archael organisms. Certain RNA ligases may also be employed in the methods of the invention.

In this ligation step, a suitable ligase and any reagents that are necessary and/or desirable are combined with the reaction mixture and maintained under conditions sufficient for ligation of the hybridized ligation oligonucleotides to occur. Ligation reaction conditions are well known to those of skill in the art. During ligation, the reaction mixture in certain embodiments may be maintained at a temperature ranging from about 20° C. to about 45° C., such as from about 25° C. to about 37° C. for a period of time ranging from about 5 minutes to about 16 hours, such as from about 1 hour to about 4 hours. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 minutes to about 16 hours, such as from about 1 hour to about 10 hours, including from about 2 to about 8 hours. In a representative embodiment, the ligation reaction mixture includes 50 mM Tris pH7.5, 10 mM $MgCl_2$, 10 mM DTT, 1 mM ATP, 25 mg/ml BSA, 0.25 units/ml Rnase inhibitor, and T4 DNA ligase at 0.125 units/ml. In yet another representative embodiment, 2.125 mM magnesium ion, 0.2 units/ml Rnase inhibitor; and 0.125 units/ml DNA ligase are employed.

Following ligation, the product ligated nucleic acid tail compounds are detected as a measure of the amount of analyte in the sample. In these embodiments, the ligated product comprises a single stranded nucleic acid linker (which is the product of the ligation of the two proximal nucleic acid domains and tails) terminating at each in a target analyte ligand domain.

The next step of the subject methods following the above-described ligation step is to determine the presence of the ligated product in the reaction mixture in order to detect the target analyte in the sample. In other words, the reaction mixture is screened, i.e., assayed, evaluated, tested, etc., for the presence of any resultant ligation products in order to detect the presence of the target analyte in the sample being assayed.

The ligated product produced by the above-described methods may, in the broadest sense, be detected using any convenient protocol. The particular detection protocol may vary depending on the sensitivity desired and the application in which the method is being practiced. In certain embodiments, the ligated product nucleic acid is directly detected without any amplification, while in other embodiments the detection protocol may include an amplification component, in which the copy number of the ligated product nucleic acid is increased, e.g., to enhance sensitivity of the particular assay. Where detection without amplification is practicable, the product ligated nucleic acid may be detected in a number of different ways. For example, one or more of the nucleic acid tails of the proximity probes may have been directly labeled, e.g., fluorescently or radioisotopically labeled, such that the ligation product is directly labeled. In these embodiments, the directly labeled ligation product may be size separated from the remainder of the reaction mixture, including unligated directly labeled ligation oligonucleotides, in order to detect the ligated nucleic acid. Alternatively, conformationally selective probes, e.g., molecular beacons (as described in greater detail below) may be employed to detect to the presence of the ligation product, where these probes are directed to a sequence that spans the ligated nucleic acids and therefore only exists in its entirety in the ligation product.

As indicated above, in certain embodiments of the subject methods, the detection step includes an amplification step, where the copy number of ligated nucleic acids is increased, e.g., in order to enhance sensitivity of the assay. The amplification may be linear or exponential, as desired, where representative amplification protocols of interest include, but are not limited to: polymerase chain reaction (PCR); isothermal amplification, etc.

The polymerase chain reaction (PCR), is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above ligated nucleic acids or ligation product (which may also be viewed as a template nucleic acid in an amplification reaction) is combined with one or more primers that are employed in the primer extension reaction, e.g., the PCR primers (such as forward and reverse primers employed in geometric (or exponential) amplification or a single primer employed in a linear amplification). The oligonucleotide primers with which the template nucleic acid (hereinafter referred to as template DNA for convenience) is contacted will be of sufficient length to provide for hybridization to complementary template DNA under annealing conditions (described in greater detail below. The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired.

In addition to the above components, the reaction mixture produced in the subject methods typically includes a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Proc. Natl. Acad. Sci. USA (1994) 91:2216-2220); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3¢®5¢ exonuclease activity, e.g., as may be provided by a Family B polymerase, where Family B polymerases of interest include, but are not limited to: *Thermococcus litoralis* DNA polymerase (Vent) as described in Perler et al., Proc. Natl. Acad. Sci. USA (1992) 89:5577; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases are present, i.e. dATP, dTTP, dCTP and dGTP. In the subject methods, each dNTP will typically be present in an amount ranging from about 10 to 5000 uM, usually from about 20 to 1000 uM.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, NH4-acetate, K-glutamate, NH4Cl, ammonium sulfate, and the like may be employed. The divalent cation may be magnesium, manganese, zinc and the like, where the cation will typically be magnesium. Any convenient source of magnesium cation may be employed, including MgCl2, Mg-acetate, and the like. The amount of Mg2+ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture of this step of the subject methods, the various constituent components may be combined in any convenient order. For example, the buffer may be combined with primer, polymerase and then template DNA, or all of the various constituent components may be combined at the same time to produce the reaction mixture.

Representative embodiments of this protocol are illustrated in FIGS. 1 to 3. In FIGS. 1 to 3, 5' primers (106, 112) generally bind to a region to provide for amplification of a target nucleic acid, and may bind to a 5' portion of the target sequence, as exemplified in FIGS. 1 to 3. 3' primers (107, 113) generally bind to a sequence that is complementary to a 3' portion of the nucleic acid generated by extension from the 5' primer, as exemplified in FIGS. 1 to 3. The 5' and 3' primers may be separated by about 10, 20, 30, 40, 50, or 60 contiguous nucleotides, usually about 30-50 contiguous nucleotides.

In some embodiments, primers for use in the assays herein are designed based on the nucleic acid sequence of the nucleic acid domain of the proximity probes (105 and 106, FIGS. 1 and 3). In other embodiments, primers for use in the assays herein are designed based on the nucleic acid sequence of supplemental nucleic acids (112 and 113, FIG. 2) that may be employed in the protocol, and described in greater detail below.

The amplified products of the amplification reaction may be detected using any convenient protocol, where the particular protocol employed may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplification product, as opposed to double stranded molecules in general, may be employed to detect the amplification. In these embodiments, the signal producing system may include a probe nucleic acid that specific binds to a sequence found in the amplification product, where the probe nucleic acid may be labeled with a directly or indirectly detectable label. A directly detectable label is one that can be directly detected without the use of additional reagents, while an indirectly detectable label is one that is detectable by employing one or more additional reagent, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labeling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labeled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labeled probe nucleic acids are labeled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others electronic structure. If the fluorescence-modifying group is a quenching group, this will result in the quenching group preventing the fluorescent group from even emitting light.

The energy transfer labeled probe nucleic acid, e.g., oligonucleotide, may be structured in a variety of different ways, so long as it includes a donor, acceptor and target nucleic acid binding domains. As such, the energy transfer labeled oligonucleotides employed in these embodiments of subject methods are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labeled probe oligonucleotides also include a target nucleic acid binding domain, which binds to a target nucleic acid sequence found in the amplification product of interest (as described above), e.g., under stringent hybridization conditions (as defined above). This target binding domain typically ranges in length from about 10 to about 60 nt, usually from about 15 to about 30 nt. Depending on the nature of the oligonucleotide and the assay itself, the target binding domain may hybridize to a region of the template nucleic acid or a region of the primer extension product. For example, where the assay is a 5' nuclease assay, e.g., in which a TaqmanÔ type oligonucleotide probe is employed, the target binding domain hybridizes under stringent conditions to a target binding site of the template nucleic acid, which is downstream or 3' of the primer binding site. In alternative embodiments, e.g., in molecular beacon type assays, the target binding domain hybridizes to a domain of a primer extension product. The overall length of the energy transfer labeled oligonucleotides employed in these embodiments, which includes all three domains mentioned above, typically ranges from about 10 to about 60 nucleotides, usually from about 15 to about 30 nucleotides.

In certain embodiments, the energy transfer labeled oligonucleotide is structured such that energy transfer occurs between the fluorophore and acceptor of the energy transfer labeled oligonucleotide probe upon fluorophore excitation when the energy transfer labeled oligonucleotide is not hybridized to target nucleic acid.

In certain embodiments, the oligonucleotide is a single stranded molecule that does not form intramolecular structures and in which energy transfer occurs because the spacing of the donor and acceptor provides for energy transfer in the single stranded linear format. In these embodiments, energy transfer also occurs between the fluorophore and acceptor of labeled oligonucleotide probe upon fluorophore excitation when the labeled oligonucleotide probe is hybridized to a target nucleic acid. Specific examples of such labeled oligonucleotide probes include the TaqmanÔ type probes, as described in U.S. Pat. No. 6,248,526, the disclosure of which is herein incorporated by reference (as well as Held et al., Genome Res. (1996) 6:986-994; Holland et al., Proc. Nat'l Acad. Sci. USA (1991) 88:7276-7280; and Lee et al., Nuc. Acids Res. (1993) 21:3761-3766 (1993)). In many of these embodiments, the target nucleic acid binding domain is one that hybridizes to, i.e., is complementary to, a sequence of the template nucleic acid, i.e., the target nucleic acid of the target nucleic acid binding domain is a sequence present in the template nucleic acid (i.e., the pseudotarget or surrogate nucleic acid).

In other embodiments, the probe oligonucleotides are structured such that energy transfer does not occur between the fluorophore and acceptor of the energy transfer labeled oligonucleotide probe upon fluorophore excitation when the energy transfer labeled oligonucleotide probe is hybridized to a target nucleic acid. Examples of these types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference). In many of these embodiments, the target binding sequence or domain comprises a hybridization domain complementary to a sequence of the primer extension product of the amplification reaction, and not to a sequence found in the pseudotarget nucleic acid.

The next step in the subject methods is signal detection from the labeled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time.

Where the detection protocol is a real time protocol, e.g., as employed in real time PCR reaction protocols, data may be collected in this way at frequent intervals, for example once every 10 ms, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signaling moiety (i.e. fluorophore). The areas under the peaks can be determined which represents the intensity value for each signal, and if required, expressed as quotients of each other. The differential of signal intensities and/or ratios will allow changes in labeled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g., as correlated to the amount of amplification product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more control nucleic analytes in the reaction mixture, as described above.

In this manner, a reaction mixture is readily screened for the presence of target analyte(s). The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc.

The methods of the subject invention may be modified in order to reduce the background associated with non-specific nucleic acid hybridization events. Such modifications include adjustments to the assay that will reduce the non-specific nucleic acid hybridization events. In some embodiments, a protein may be added to the mixture containing the sample and the proximity probes in order to reduce weak and non-specific DNA hybridization event. For example, E. coli single strand DNA binding protein has been used to increase the yield and specificity of primer extension reactions and PCR reactions. (U.S. Pat. Nos. 5,449,603 and 5,534,407.) The gene 32 protein (single strand DNA binding protein) of phage T4 apparently improves the ability to amplify larger DNA fragments (Schwartz, et al., Nucl. Acids Res. 18: 1079 (1990)) and enhances DNA polymerase fidelity (Huang, DNA Cell. Biol. 15: 589-594 (1996)). When employed, such a protein will be used to achieve a concentration in the reaction mixture that ranges from about 0.01 ng/uL to about 1 ug/uL; such as from about 0.1 ng/uL to about 100 ng/uL; including from about 1 ng/uL to about 10 ng/uL. In certain embodiments, the subject methods employ single strand binding protein but do not employ asymmetric connectors, as described above. As such, included in certain embodiments of the subject methods are proximity probe assays, such as those described in the relevant literature section, that employ a symmetric connector, where the assay further employs single strand binding protein.

In other embodiments, double stranded nucleic acid may be used as the nucleic acid domain of the proximity probes in order to reduce weak and non-specific DNA hybridization event.

In some embodiments, the subject methods include the addition of two or more populations of supplementary nucleic acids (110 and 111) that are complementary to the nucleic acid domains (104 and 105) of the proximity probes in a region adjacent to the region of complementarity of the asymmetric nucleic acid connectors (108 and 109). In such embodiments, the proximity dependant interaction between the proximity probes may be detected by designing nucleic acid amplification primers (112 and 113) complementary to the supplementary nucleic acids (110 and 111) allowing for decreased background associated with non-specific nucleic acid amplification. When employed, these supplemental nucleic acids typically range in length from about 10 to about 100, such as from about 15 to about 75, including from about 20 to about 50. The supplemental nucleic acids are employed in an amount that achieves a concentration in the reaction mixture that ranges from about 1 pM to about 1 mM, including from about 1 nM to about 1 µM.

In some embodiments, the subject methods include proximity probes that include binding domains that directly interact with the target analyte. In such embodiments, the analyte binding domains of the proximity probes interact directly by directly binding to binding domains, e.g., epitopes, on the target analyte.

In other embodiments, the subject methods include proximity probes that include binding domains that indirectly interact with the target analyte. In such embodiments, the proximity probes interact indirectly with a target analyte by binding to a third binding moiety, which third binding moiety binds to a binding site of the target analyte. In such embodiments, proximity probes may be designed such that the binding domains are capable of binding many different third binding moieties. In such embodiments, the third binding moiety is incubated with the analyte and then the proximity probes specific to the third binding moiety are added and allowed to preferentially react when in a high local concentration.

In the case of detecting an analyte with proximity-probes of low affinity and slow binding kinetics, a preincubation step with the proximity-probes at a sufficiently high concentration promotes binding of the proximity probes to the analyte. This preincubation step may be quickly diluted in a large volume of cold buffer (e.g., buffer that does not include the analyte or the proximity probes), and a portion of this dilution subsequently added to a ligation reaction mixture. This ligation reaction mixture contains the asymmetric connectors, ATP and ligase enzyme. The low temperature, e.g., ranging from about 0 to about 20° C., including from about 4 to about 10° C., minimizes the dissociation of existing proximity-probe-analyte complexes while the vast dilution, results in a decrease of the concentration of the unbound proximity-probes, thereby lowering their reactivity and minimizing the background signal.

In such embodiments, the assay is performed by using a small incubation volume of from about 1 µl to about 7 µl, such as about 1 µl, or about 2 µl, or about 3 µl, or about 4 µl, or about 5 µl or about 6 µl, of sample and proximity probes and then adding the connectors in a larger incubation volume of from about 8 µl to about 1.5 ml or more, such as form about 20 µl to about 1.3 ml, such as from about 50 µl to about 1 ml, such as from about 75 µl to about 800 µl, such as form about 100 µl to about 500 µl, such as from about 200 µl to about 300 µl. The effective concentration of the proximity probes in the final incubation volume is thus diluted, reducing the background while maintaining the signal since a new binding equilibrium between the probes and analyte does not have time to form before hybridization of the connectors. This approach enables an unlimited sensitivity as long as the ligation products can be concentrated from the larger volumes, such as over 100 µl or more and then detecting the proximity dependent interaction. In such embodiments, the probe-probe interactions can be eliminated by using single strand binding proteins.

Problems associated with complex samples may be addressed by diluting the complex sample prior to the analysis. This will greatly decrease the amount of proteins the probes may bind unspecifically to thereby lowering concentration of probes required. While the analyte will also be diluted, the high sensitivity of the proximity probing will provide good detection and quantification.

The above-described protocol results in detection of connector mediated proximity dependent interactions that are present in the reaction mixture, which in turn provides a measure of the amount of target analyte in the sample being assayed. The measure may be qualitative or quantitative, where quantitative refers to both relative and absolute quantitative determinations. Accordingly, the above described methods of detecting the presence of one or more target analytes in a complex sample finds use in a variety of different applications, representative ones of which are now reviewed in greater detail.

Utility

The subject methods may be used to screen a sample for the presence or absence of one or more target analytes in a sample. As indicated above, the invention provides methods of detecting the presence of one or more target analytes in a sample. In the broadest sense, the method may be qualitative or quantitative. As such, where detection is qualitative, the methods provide a reading or evaluation, e.g., assessment, of whether or not the target analyte is present in the sample being assayed. In yet other embodiments, the methods provide a quantitative detection of whether the target analyte is present in the sample being assayed, i.e., an evaluation or assessment of the actual amount of the target analyte in the sample being assayed. In such embodiments, the quantitative detection may be absolute or, if the method is a method of detecting two or more different target analytes in a sample, relative. As such, the term "quantifying" when used in the context of quantifying a target analyte(s) in a sample can refer to absolute or to relative quantification. Absolute quantification may be accomplished by inclusion of known concentration(s) of one or more control analytes and referencing the detected level of the target analyte with the known control nucleic acids (e.g., through generation of a standard curve). Alternatively, relative quantification can be accomplished by comparison of detected levels or amounts between two or more different target analytes to provide a relative quantification of each of the two or more different analytes, e.g., relative to each other.

The subject methods can be employed to detect the presence of one or more target analytes in a variety of different types of samples, including complex samples having large amounts of non-target entities, where the subject methods provide for detection of the target analytes(s) with high sensitivity. As such, the subject methods are highly sensitive methods of detecting one or more target analytes in a simple or complex sample. The sample that is assayed in the subject methods is in many embodiments from a physiological source. The physiological source may be eukaryotic or prokaryotic, with physiological sources of interest including sources derived from single celled organisms such as bacteria and yeast and multicellular organisms, including plants and animals, particularly mammals, where the physiological sources from multicellular organisms may be derived from particular organs or tissues of the multicellular organism, or from isolated cells or subcellular/extracellular fractions derived therefrom.

The methods of the present invention may be used to detect a wide variety of analytes. Typically, the target analytes that are detectable by the subject methods are ones that at least two proximity probes can bind to at the same time. In some embodiments, the binding sites of the analyte are the same, i.e., the binding sites bind the same binding domain. In other embodiments, the binding sites are distinctly different, i.e., each binding site bind a distinctly different binding domain.

Analytes of interest can be a proteinacious molecules, such as, but not limited to, proteinacious analytes, including peptides and proteins and fragments thereof, as well as prions and other proteinaceous types of analytes, where the analytes may be a single molecule, a complex that includes two or more molecular subunits, which may or may not be covalently bound to each other, a microorganism, e.g., virus or single celled pathogen, a cell, a multicellular organism or portion thereof, and the like. Since the length of the nucleic acid domain of the proximity probes can be constructed to span varying molecular distances, analyte binding sites need not be on the same molecule. However, they may be on separate, but closely positioned, molecules. For example, the multiple binding domains of an organism, such as a virus, bacteria or cell can be targeted by the methods of the present invention.

In addition, the subject methods may also be used to screen for compounds that modulate the interaction between the binding domain of the proximity probe with the binding region of the analyte. The term modulating includes both decreasing (e.g., inhibiting) and enhancing the interaction between the two molecules. The screening method may be an in vitro or in vivo format, where both formats are readily developed by those of skill in the art.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in the a variety of methods, including methods of modulating the activity of the target analyte, and conditions related to the presence and/or activity thereof.

Kits

Also provided are kits that find use in practicing the subject methods, as described above. For example, in some embodiments, kits for practicing the subject methods include at one set of proximity probes, which proximity probes each include an analyte binding domain and a nucleic acid binding domain as described above. As indicated above, the certain protocols will employ two or more different sets of such probes for simultaneous detection of two or more target analytes in a sample, e.g., in multiplex and/or high throughput formats. As such, in certain embodiments the kits will include two or more distinct sets of proximity probes. The kits also may include at least a pair of corresponding asymmetric connectors or splints, as described above. Furthermore, additional reagents that are required or desired in the protocol to be practiced with the kit components may be present, which additional reagents include, but are not limited to: a ligase, pairs of supplementary nucleic acids, single strand binding proteins, and PCR amplification reagents (e.g., nucleotides, buffers, cations, etc.), and the like. In certain embodiments, the kits may include elements employed in reducing the effective volume of an incubation mixture, as reviewed above, e.g., a volume excluder. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems that find use in practicing the subject methods, as described above. For example, in some embodiments, systems for practicing the subject methods may include at least one set or proximity probes; a least one pair of asymmetric connectors; and a nucleic acid ligase. Furthermore, additional reagents that are required or desired in the protocol to be practiced with the system components may be present, which additional reagents include, but are not limited to: pairs of supplementary nucleic acids, single strand binding proteins, and PCR amplification reagents (e.g., nucleotides, buffers, cations, etc.), and the like. In certain embodiments, the system may include elements employed in reducing the effective volume of an incubation mixture, as reviewed above, e.g., a volume excluder, a controlled evaporation device, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following materials and methods are used in the examples below.

Proximity Probes

A model system for proximity ligation was used to investigate the effects of using a single strand binding protein and the asymmetric connectors. A proximity probe pair was constructed for the detection of the analyte streptavidin. The model proximity probes designed to detect the analyte streptavidin included a biotin binding domain linked to a ligatable nucleic acid domain. Two proximity probes were constructed, the first proximity probe included a nucleic acid domain that had a 3' free end and the second proximity probe included a nucleic acid domain that had a 5' free end.

Streptavidin is a tetrameric protein capable of binding four biotin molecules or in this case up to four proximity probes, which proximity probes included a biotin binding domain and a nucleic acid domain. The nucleic acid sequences of the nucleic acid domains of the proximity probed were as follows:

```
3'-free proximity probe
                                                         (SEQ ID NO: 01)
Biotin-teg-c18-c18-c18-c18-CATCGCCCTTGGACTAGCATATCTAAATCGTG 5'-free proximity probe
                                                         (SEQ ID NO: 02)
Phosphate-TCGTGTCTAATATCGTTACCTTGATTCCCGTCC-c18-c18-c18-c18-teg-biotin
```

Symmetric Connectors

Symmetric connectors were designed such that the 3' end of the symmetric connector had a region of complementarity to the 3' end of the nucleic acid domain of the 3'-free proximity probe and the 5' end of the connector had a region of complementarity to the 5' end of the nucleic acid domain of the 5'-free proximity probe. The region of complementarity of such symmetric connectors to the nucleic acid domains of the proximity probes is symmetrical. That is, the number of nucleotides in the symmetrical connectors that is complementary to the 5' end of the nucleic acid domain of the 5'-free proximity probe is equal to the number of nucleotides to which the symmetrical connector is complementary to the 3' end of the nucleic acid domain of the 3'-free proximity probe.

The symmetric connector 10+10 connector has a region of complementarity of ten nucleotides at the 5' end of the connector to the 5' end of the nucleic acid domain of the 5'-free proximity probe and a region of complementarity of ten nucleotides at the 3' end of the connector to the 3' end of the nucleic acid domain of the 3'-free proximity probe.

The symmetric connector 20+20 connector has a region of complementarity of twenty nucleotides at the 5' end of the connector to the 5' end of the nucleic acid domain of the 5'-free proximity probe and a region of complementarity of twenty nucleotides at the 3' end of the connector to the 3' end of the nucleic acid domain of the 3'-free proximity probe. The symmetric connector 20+20 contained uracils in order to enable its degradation prior to PCR so that it could not hybridize during the PCR itself.

The symmetric connectors that were used in the examples were as follows:

```
Symmetric Connector 10 + 10
                                          (SEQ ID NO: 03)
5'-TACTTAGACACGACACGATTTAGTTT-3'

Symmetric Connector 20 + 20
                                          (SEQ ID NO: 04)
5'-GGTAACGAUAUUAGACACGACACGAUUUAGAUAUGCUAGT-3'
```

Asymmetric Connectors

Asymmetric connectors were designed such that the 3' end of the symmetric connector had a region of complementarity to the 3' end of the nucleic acid domain of the 3'-free proximity probe and the 5' end of the connector had a region of complementarity to the 5' end of the nucleic acid domain of the 5'-free proximity probe. The region of complementarity of such asymmetric connectors to the nucleic acid domains of the proximity probes is asymmetrical. That is, the number of nucleotides to which the asymmetrical connector is complementary to the 5' end of the nucleic acid domain of the 5'-free proximity probe is not equal to the number of nucleotides that the asymmetrical connectors is complementary to the 3' end of the nucleic acid domain of the 3'-free proximity probe.

The asymmetric connectors contained uracils in order to enable the degradation of the asymmetric connectors prior to PCR so that the connectors could not hybridize during the PCR itself. The asymmetric connectors also contained a number of mismatched nucleotides at each end to reduce the probability of the connectors acting as primers.

The asymmetric connector 20+10 connector has a region of complementarity of twenty nucleotides at the 5' end of the connector to the 5' end of the nucleic acid domain of the 5'-free proximity probe and a region of complementarity of ten nucleotides at the 3' end of the connector to the 3' end of the nucleic acid domain of the 3'-free proximity probe.

The asymmetric connector 10+20 connector has a region of complementarity of ten nucleotides at the 5' end of the connector to the 5' end of the nucleic acid domain of the 5'-free proximity probe and a region of complementarity of twenty nucleotides at the 3' end of the connector to the 3' end of the nucleic acid domain of the 3'-free proximity probe.

The asymmetric connector 15+10 connector has a region of complementarity of fifteen nucleotides at the 5' end of the connector to the 5' end of the nucleic acid domain of the 5'-free proximity probe and a region of complementarity of ten nucleotides at the 3' end of the connector to the 3' end of the nucleic acid domain of the 3'-free proximity probe.

The asymmetric connector 10+15 connector has a region of complementarity of ten nucleotides at the 5' end of the connector to the 5' end of the nucleic acid domain of the 5'-free proximity probe and a region of complementarity of fifteen nucleotides at the 3' end of the connector to the 3' end of the nucleic acid domain of the 3'-free proximity probe.

The asymmetric connectors that were used in the examples were as follows:

```
Asymmetric Connector 20 + 10
                                          (SEQ ID NO: 05)
5'-ATT^GGUAACGAUAUUAGACACGACACGAUUUAG^TAT-3'

Asymmetric Connector 10 + 20
                                          (SEQ ID NO: 06)
5'-TAT^UUAGACACGACACGAUUUAGAUAUGCUAGU^AAT-3'

Asymmetric Connector 15 + 10
                                          (SEQ ID NO: 07)
5'-ATT^CGAUAUUAGACACGACACGAUUUAG^TAT-3'

Asymmetric Connector 10 + 15
                                          (SEQ ID NO: 08)
5'-TAT^UUAGACACGA CACGAUUUAG AUAUG^AAT-3'
```

Proximity Dependent Interaction

All experiments were carried out by first incubating the two proximity probes with the target analyte streptavidin at 37° Celsius for one hour to reach binding equilibrium in a 5 µL volume (20 mM Tris-HCl pH 7.3, 150 mM NaCl, 0.1% BSA or 1% BSA). 15 µL of the ligation mix was then added containing 0.1 Units of Ampligase (Epicentre), 0.3 mM NAD, 2 mM MgCl, in a 1×PCR buffer II (Applied biosystems) and splints (i.e., connectors) of varying concentrations and design. Ligation proceeded for 30 minutes at 37° Celsius.

Detection of Proximity Dependant Interaction

The proximity dependant interaction of the proximity probes was detected by PCR. The 30 µL PCR mix was added last making a total volume of 50 µL. This mix contained 25 µL of a real-time PCR master mix (product #4304437 Applied Biosystems, Foster City Calif.), supplemented with SYBR green I dye (Molecular Probes, Eugene Oreg.) to a final dilution of 0.15×, and forward and reverse PCR-primers to a final concentration of 400 nM. The PCR master mix from ABI contains ROX internal fluorescence standard, polymerase, dNTP's, magnesium, and Amperase. Amperase is the Uracil-N-glycosylase enzyme which breaks down uracil containing DNA that is found in some of the connectors that were used. The longer connectors contained uracil residues in order to enable their degradation prior to PCR so they can not hybridize during the PCR itself. Short connectors like the symmetric connectors 10+10 do not need to be degraded since they have low hybridization efficiency at the elevated temperature of the PCR. Connectors also contained a number of mismatched nucleotides at each end to reduce the probability of the connectors as acting as primers.

PCR was performed on an ABI 7700 with the following temperature profile:
37° C. (5 min)
50° C. (10 min)
95° C. (10 min)
[95° C. (15 sec)–60° C. (1 min)]×45 times.
Sybr green fluorescence was read at the 60 degrees point.
The PCR primers that were used were as follows:

```
Forward primer, PCR
CATCGCCCTTGGACTAGCAT        (SEQ ID NO: 09)

Reverse primer, PCR
CCTCGGGAATCAAGGTAACG        (SEQ ID NO: 10)
```

Example 1

Effect of SSB on Background in Proximity Assay

The single strand binding protein (SSB) from *E. coli* was assessed for its potential to remove weak probe to probe interactions and thereby reduce background resulting from non specific probe-probe interactions. The experiment was performed with or without 5 ng/μL SSB (United States Biochemical, Cleveland Ohio) in 2 μL incubations with 100 pM of the proximity probes with 1% BSA, ligated in 20 μL with 1 μM of the first and second asymmetric connectors, and amplified by real-time PCR in 50 μL.

The connectors used in the experiment included: (1) the asymmetric connector 10+15; and (2) the asymmetric connector 15+10.

Figure 4:
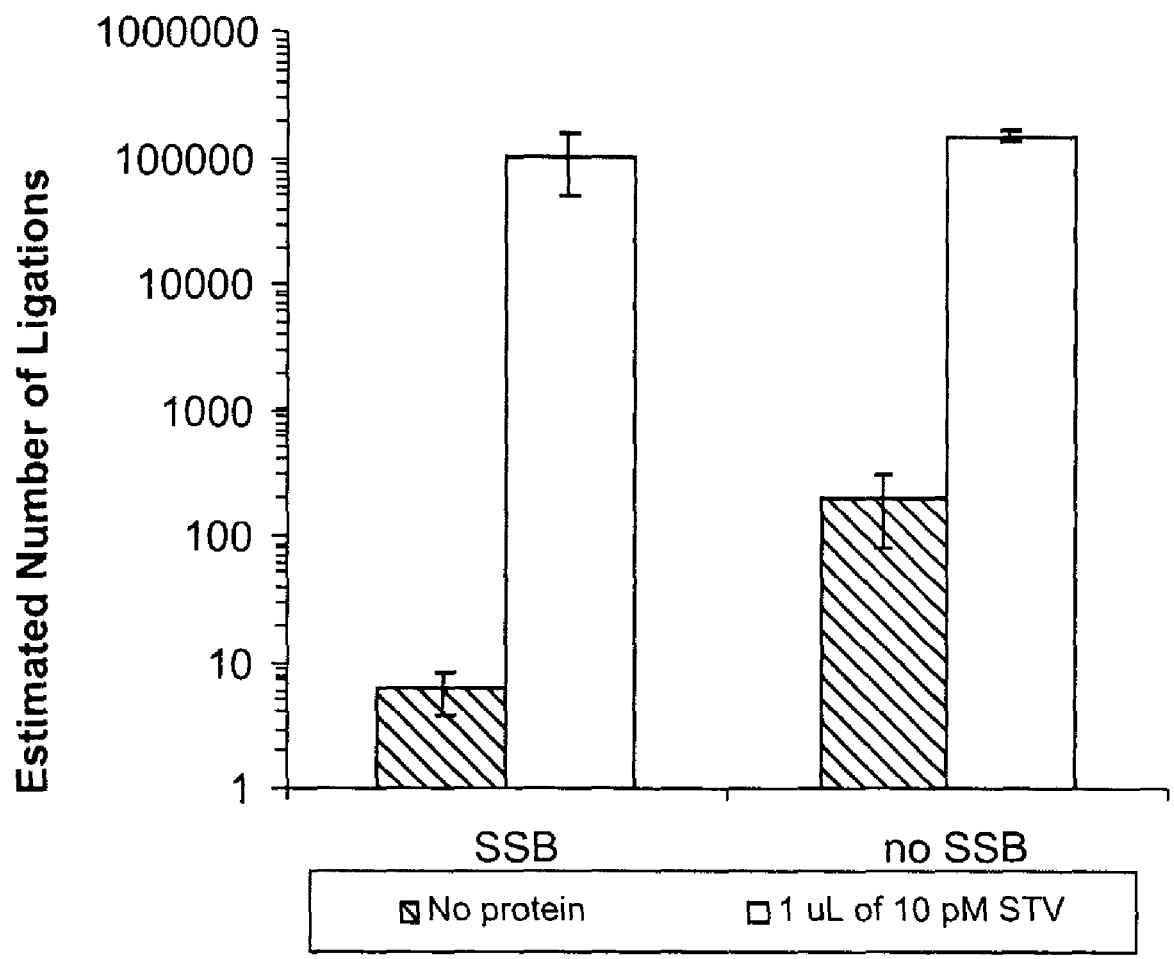
FIG. 4 is a bar graph showing the results of proximity probing experiments performed in the presence of single strand binding protein and absence of single strand binding protein.

As shown in FIG. 4, the inclusion of SSB in the assay resulted in a reduction of the background by over 10-fold as compared to the assay that that did not include the SSB. Moreover, FIG. 3 also shows that the overall signal was not affected by the inclusion of the SSB.

Example 2

Comparison of Connector Types for Background Reduction

In order to compare the effect of different connector types on the reduction of background, an experiment was performed with various connector types all at 1 μM concentration in a 20 μL ligation. The incubation of proximity probes with sample was performed in 5 uL volume with 50 pM proximity probes, 5 ng/uL SSB, and 1% BSA.

The different connector types that were examined included: (1) the asymmetric connector 10+20; (2) the asymmetric connector 20+10; (3) the symmetric connector 20+20; and (4) the symmetric connector 10+10.

Figure 5:
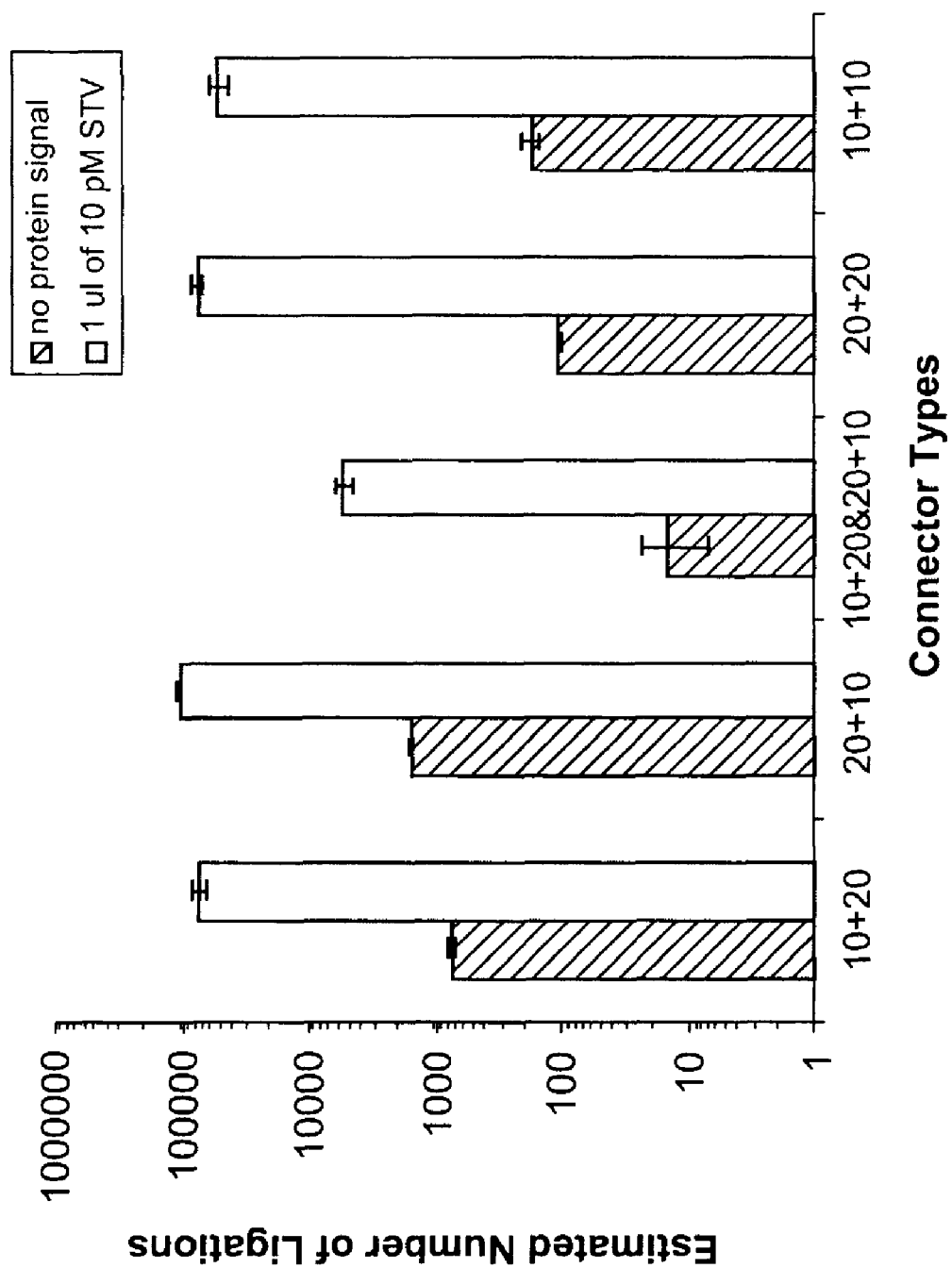
FIG. 5 is a bar graph showing the results of proximity probing experiments using symmetric connectors, asymmetric connectors, and combinations of different asymmetric connectors.

As seen in FIG. 5, the use of the combination of the two asymmetric connectors 10+20 and 20+10 showed a significant reduction in the background as compared to the other combinations of the connectors. However, the use of two asymmetric connectors 10+20 and 20+10 also showed a reduction in the overall signal as well, as compared to the other combinations of connectors Example 3

Asymmetric Connectors with 10+15 and 15+10 Design

In order to assess the lower degree of hybridization stability in the asymmetry between the two splints (i.e., connectors) used for optimal decrease in background, an experiment was performed with adjusted regions of complementarity. The experiment was performed with various connector types all at 1 μM concentration in a 20 μL ligation. The incubation of proximity probes with sample was performed in 5 uL volume with 50 pM proximity probes, 5 ng/uL SSB, and 1% BSA.

The connectors used in the experiment included: (1) the asymmetric connector 10+15; (2) the asymmetric connector 15+10; and (3) the symmetric connector 20+20 connector.

Figure 6:
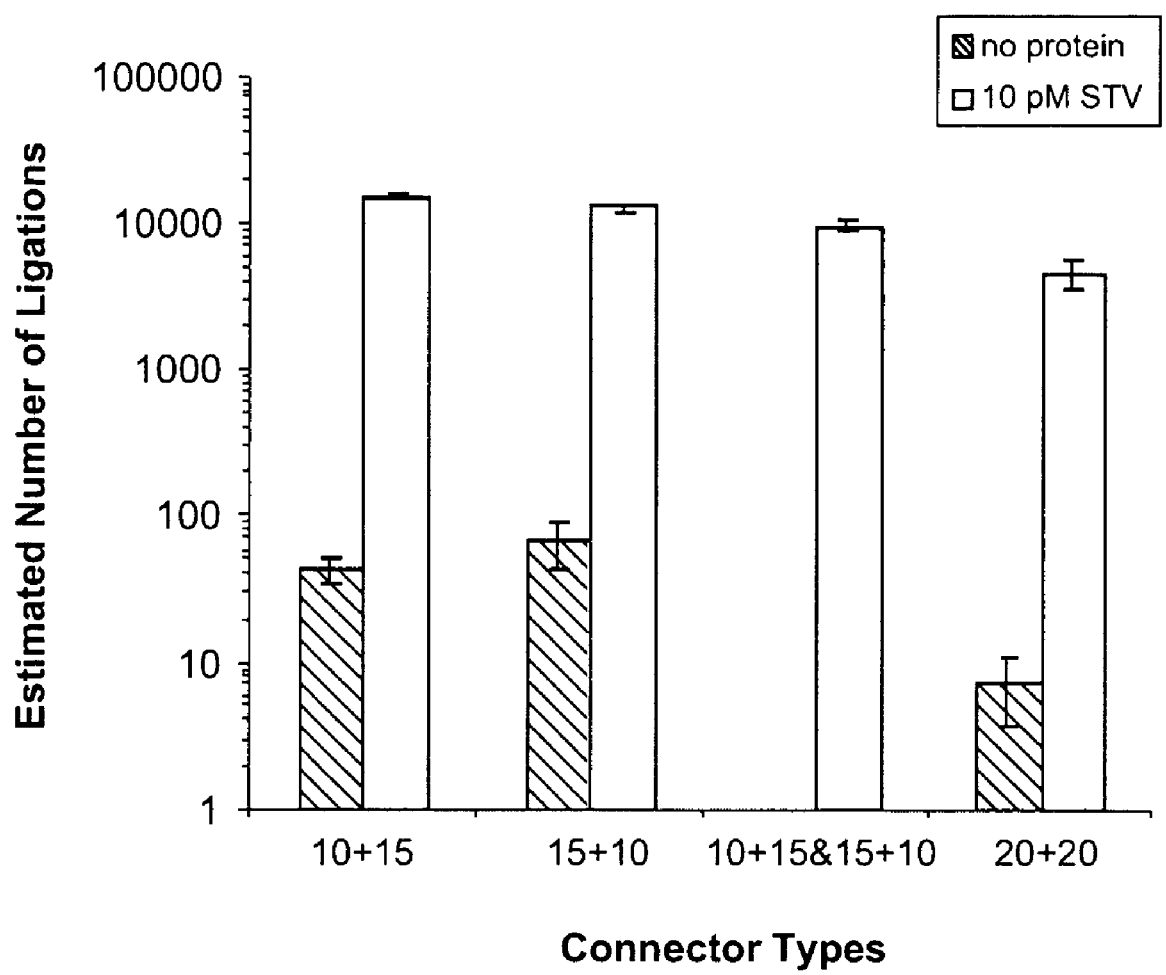
FIG. 6 is a bar graph showing the results of proximity probing experiments using varying combinations of asymmetric connectors compared to symmetric connectors.

As shown in FIG. 6, the combination of the two asymmetric connectors did not significantly reduce the overall signal of the assay. However, the use of the two asymmetric connectors, specifically the 10+15 and 15+10 did reduce the background to a level not even detectable in this particular experiment.

Example 4

Standard Curve of Serially Diluted Streptavidin

Serially diluted samples of straptavidin were used in order to assess the capability of the assay to detect analyte in a sample. Serially diluted concentrations of streptavidin were added to incubations totalling 2 μL, containing 100 pM of the proximity probes, 0.1% BSA and 5 ng/μL SSB. The ligation mix contained 1 μM each of the two assymetric connectors 10+15 and 15+10.

The connectors used in the experiment included: (1) the asymmetric connector 10+15; and (2) the asymmetric connector 15+10.

Figure 7:
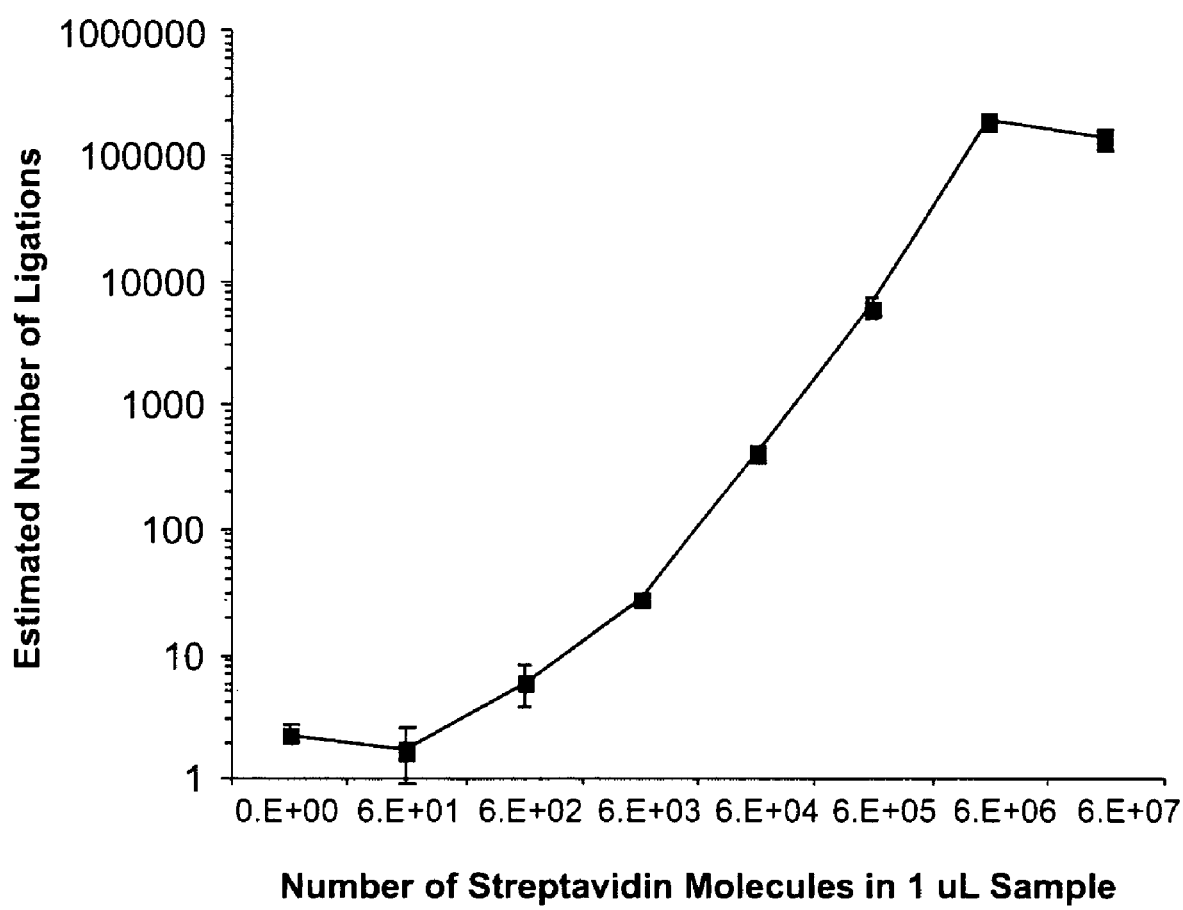
FIG. 7 shows the detection of strapavidin at varying concentrations using proximity probes and asymmetric connectors.

As seen in FIG. 7 the assay is capable of detecting the target protein down to a 1 μL sample at a 1 fM concentration. Such a detection level corresponds to 600 protein molecules or 1 zepto mole in the sample.

It is evident from the above results and discussion that the subject inventions provides for greatly improved proximity based assays which can be employed to detect the present of one or more target analytes in a sample with high sensitivity. Accordingly, the subject invention represents a significant contribution to the art.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for detecting an analyte in a sample comprising:
   (a) producing a mixture by combining said sample and at least one set of at least first and second proximity probes each comprising an analyte binding domain and a nucleic acid binding domain, wherein said first and second proximity probes can simultaneously bind to said analyte;
   (b) combining said mixture with:
      (i) a first asymmetric connector comprising a first region of complementarity for said nucleic acid binding domain of said first proximity probe and a second region of complementarity for said nucleic acid binding domain of said second proximity probe, wherein said first region is longer that said second region; and
      (ii) a second asymmetric connector comprising a first region of complementarity for said nucleic acid binding domain of said second proximity probe and a second region of complementarity for said nucleic acid binding domain of said first proximity probe, wherein said first region is longer than said second region;
   wherein said first and second asymmetric connectors have substantially opposite binding characteristics with respect to said first and second proximity probes and with respect to each other; and
   (c) detecting a connector mediated proximity dependent interaction between said first and second proximity probes to detect the presence of said analyte in said sample.

2. The method according to claim 1, wherein said mixture is subjected to nucleic acid ligation conditions.

3. The method according to claim 2, wherein said proximity dependant interaction is a ligation event between said nucleic acid binding domain of first and second proximity probes.

4. The method according to claim 1, wherein said mixture further comprises a single strand binding protein.

5. The method according to claim 1, wherein said method further comprises reducing the effective volume of said mixture prior to step (b).

6. The method according to claim 5, wherein said effective volume is reduced by the presence of a volume excluder.

7. The method according to claim 6, wherein said volume exclude is a PEG polymer.

8. The method according to claim 5, wherein said effective volume is reduced by removing water from said mixture.

9. The method according to claim 8, wherein water is removed by evaporation.

10. The method according to claim 1, wherein said detecting employs a polymerase chain reaction (PCR) protocol.

11. The method according to claim 1, wherein said analyte binding domain is an antibody or binding fragment thereof.

12. The method according to claim 1, where said method employs a single set of proximity probes.

13. The method according to claim 1, wherein method employs two or more sets of proximity probes.

14. The method according to claim 1, wherein said detecting is qualitative.

15. The method according to claim 1, wherein said detecting is quantitative.

16. The method according to claim 1, wherein said first region of said first asymmetric connector is at least about 5 nucleotides longer than said second region.

17. The method according to claim 1, wherein said first region of said first asymmetric connector is from about 13 to 17 nucleotides in length and said second region is from about 8 to 12 nucleotides in length.

18. The method according to claim 1, wherein said first region of said second asymmetric connector is at least about 5 nucleotides longer that said second region.

19. The method according to claim 1, wherein said first region of said second asymmetric connector is from about 13 to 17 nucleotides in length and said second region is from about 8 to 12 nucleotides in length.

20. The method according to claim 1, wherein the analyte is a peptide.

21. The method according to claim 1, wherein said analyte is a prion.

22. The method according to claim 1, wherein said analyte comprises a single molecule.

23. The method according to claim 1, wherein said analyte comprises two non-covalently bound molecules.

24. The method according to claim 1, wherein said proximity probes bind to said analyte indirectly.

25. The method according to claim 1, wherein said proximity probes bind to said analyte directly.

26. A method for detecting an analyte in a sample comprising:
   (a) producing a mixture by combining:
      (i) said sample;
      (ii) at least one set of at least first and second proximity probes each comprising an analyte binding domain and a nucleic acid binding domain, wherein said first and second proximity probes can simultaneously bind to said analyte; and
      (iii) a single strand binding protein;
   (b) combining said mixture with at least two asymmetric connectors corresponding to said first and second proximity probes; and
   (c) detecting a connector mediated proximity dependent interaction between said first and second proximity probes to detect the presence of said analyte in said sample.

27. A method for detecting an analyte in a sample comprising:
   (a) producing a mixture by combining said sample and at least one set of at least first and second proximity probes each comprising an analyte binding domain and a nucleic acid binding domain, wherein said first and second proximity probes can simultaneously bind to said analyte;
   (b) reducing the effective volume of said mixture to increase the concentration of said proximity probes and said analyte in said mixture;
   (c) combining said mixture with at least two asymmetric connectors corresponding to said first and second proximity probes; and
   (d) detecting a connector mediated proximity dependent interaction between said first and second proximity probes to detect the presence of said analyte in said sample.

28. The method according to claim 27, wherein the effective volume of said mixture is reduced by adding a volume excluder to said mixture.

29. The method according to claim 28, wherein the volume excluder is a water soluble macromolecule material.

30. The method according to claim 27, wherein said effective volume of said mixture is reduced by removing water from said mixture.

31. The method according to claim 30, wherein said water is removed by evaporation.

32. The method according to claim 1, wherein said asymmetric connectors comprise a 3' region of complementarity and a 5' region of complementarity, wherein said 3' region of complementarity is complementary for the nucleic acid domain at the 5' terminus of the 5' free proximity probe and said 5' region of complementarity is complementary for the nucleic acid domain at the 3' terminus of the 3' free proximity probe.

33. The method according to claim 29, wherein said water soluble macromolecule material is a PEG polymer.

* * * * *